(12) United States Patent
Belcher et al.

(10) Patent No.: US 7,374,893 B2
(45) Date of Patent: May 20, 2008

(54) PEPTIDE MEDIATED SYNTHESIS OF METALLIC AND MAGNETIC MATERIALS

(75) Inventors: Angela M. Belcher, Lexington, MA (US); Brian D. Reiss, Boston, MA (US); Chuanbin Mao, Austin, TX (US); Daniel J. Solis, Boston, MA (US)

(73) Assignee: Board of Regents, University of Texas System-, Austin, TX (US)

( * ) Notice: Subject to any disclaimer, the term of this patent is extended or adjusted under 35 U.S.C. 154(b) by 0 days.

(21) Appl. No.: 11/778,713

(22) Filed: Jul. 17, 2007

(65) Prior Publication Data

US 2007/0287174 A1 Dec. 13, 2007

Related U.S. Application Data

(63) Continuation of application No. 10/665,721, filed on Sep. 22, 2003, now abandoned.

(60) Provisional application No. 60/411,804, filed on Sep. 18, 2002.

(51) Int. Cl.
*G01N 33/53* (2006.01)
*C07H 21/04* (2006.01)

(52) U.S. Cl. ............................ 435/7.1; 435/6; 435/5; 435/4; 435/DIG. 4; 435/DIG. 3; 435/DIG. 2; 435/DIG. 1; 530/300

(58) Field of Classification Search ................ 435/7.1, 435/6, 5, 4, DIG. 1–DIG. 4; 530/300
See application file for complete search history.

(56) References Cited

U.S. PATENT DOCUMENTS

| | | | |
|---|---|---|---|
| 4,593,002 | A | 6/1986 | Dulbecco |
| 5,223,409 | A | 6/1993 | Ladner et al. |
| 5,262,176 | A | 11/1993 | Palmacci et al. |
| 5,264,563 | A | 11/1993 | Huse |
| 5,270,170 | A | 12/1993 | Schatz et al. |
| 5,316,922 | A | 5/1994 | Brown et al. |
| 5,403,484 | A | 4/1995 | Ladner et al. |
| 5,510,240 | A | 4/1996 | Lam et al. |
| 5,571,698 | A | 11/1996 | Ladner et al. |
| 5,585,646 | A | 12/1996 | Kossovsky et al. |
| 5,683,867 | A | 11/1997 | Biesecker et al. |
| 5,714,330 | A | 2/1998 | Brenner et al. |
| 5,723,323 | A | 3/1998 | Kauffman et al. |
| 5,739,305 | A | 4/1998 | Cubicciotti |
| 5,750,373 | A | 5/1998 | Garrard et al. |
| 5,751,018 | A | 5/1998 | Alivisatos et al. |
| 5,763,192 | A | 6/1998 | Kauffman et al. |
| 5,814,476 | A | 9/1998 | Kauffman et al. |
| 5,817,483 | A | 10/1998 | Kauffman et al. |
| 5,821,047 | A | 10/1998 | Garrard et al. |
| 5,824,514 | A | 10/1998 | Kauffman et al. |
| 5,837,500 | A | 11/1998 | Ladner et al. |
| 5,859,210 | A | 1/1999 | Stowolitz et al. |
| 5,866,363 | A | 2/1999 | Pieczenik |
| 5,985,353 | A | 11/1999 | Lawton et al. |
| 5,990,479 | A | 11/1999 | Weiss et al. |
| 6,040,136 | A | 3/2000 | Garrard et al. |
| 6,100,035 | A | 8/2000 | Kauffman et al. |
| 6,207,392 | B1 | 3/2001 | Weiss et al. |
| 6,235,540 | B1 | 5/2001 | Siiman et al. |
| 6,329,209 | B1 | 12/2001 | Wagner et al. |
| 6,413,723 | B1 | 7/2002 | Kauffman et al. |
| 6,417,340 | B1 | 7/2002 | Mirkin et al. |
| 6,423,538 | B1 | 7/2002 | Wittrup et al. |
| 6,472,147 | B1 | 10/2002 | Janda et al. |
| 6,492,107 | B1 | 12/2002 | Kauffman et al. |
| 6,569,641 | B1 | 5/2003 | Kauffman et al. |
| 2001/0008759 | A1 | 7/2001 | Marks et al. |
| 2002/0107179 | A1 | 8/2002 | Potts et al. |
| 2003/0068900 | A1 | 4/2003 | Belcher et al. |
| 2003/0073104 | A1 | 4/2003 | Belcher et al. |
| 2003/0113714 | A1 | 6/2003 | Belcher et al. |
| 2003/0148380 | A1 | 8/2003 | Belcher et al. |
| 2004/0171139 | A1 | 9/2004 | Belcher et al. |

FOREIGN PATENT DOCUMENTS

| | | |
|---|---|---|
| WO | WO 91/14696 | 10/1991 |
| WO | WO 99/13313 | 3/1999 |
| WO | WO 02/48701 | 6/2002 |
| WO | WO 03/029431 A | 4/2003 |
| WO | WO 03/078451 | 9/2003 |
| WO | WO 2004/033488 | 4/2004 |

OTHER PUBLICATIONS

Abbott et al., Service, Symposium G, Nov. 29-Dec. 13, 1999, p. 144, GS-13.
Alivisatos, A. P. et al., Organization of 'nanocrystal molecules' using DNA, Nature, 1996, 382: pp. 609-611.
Ball, P., It all falls into place, Nature, 2001, 413: pp. 667-668.
Belcher et al., "Control of Crystal Phase Switching and Orientation by Soluble Mollusc-Shell Proteins," Letters to Nature, vol. 381, May 2, 1996, pp. 56-58.
Bergshoef, M. M. et al., Transparent nanocomposites with ultrathin, electrospun nylon-4,6 fiber reinforcement, Advanced Materials, 1999, 11: pp. 1362-1365.
Booy, F. P. et al., Cryo-electron microscopy reveals macromolecular organization within biological liquid cyrstals seen in the polarizing microscope, Int. J. Biol. Macromol, 1985, 7: pp. 327-335.
Braun, P. V. et al., Nanostructure templating in inorganic solids with organic lyotropic liquid crystals, J. Am. Chem. Soc., 1999, 121: pp. 7302-7309.

(Continued)

*Primary Examiner*—T. D. Wessendorf
(74) *Attorney, Agent, or Firm*—Foley & Lardner LLP

(57) ABSTRACT

The present invention includes methods for producing magnetic nanocrystals by using a biological molecule that has been modified to possess an amino acid oligomer that is capable of specific binding to a magnetic material.

7 Claims, 14 Drawing Sheets

OTHER PUBLICATIONS

Brott et al., "Ultrafast Holographic Nanopatterning of Biocatalytically Formed Silica," Letters to Nature, vol. 413, Sep. 2001, pp. 291-293.
Brown et al., "A Genetic Analysis of Crystal Growth," J. Mol. Biol., vol. 299, Academic Press, 2000, pp. 725-735.
Brown, S., Engineered Iron Oxide-Adhesion Mutants of the *Escherichia coli* Phase λ Receptor, 1992, 89: pp. 8651-8655.
Brown, S., Metal-recognition by repeating polypeptides, Nature Biotechnology, 1997, 15: pp. 269-272.
Chen, J. T. et al., Self-assembled smectic phases in rod-coil block copolymers, Science, 1996, 273: pp. 343-346.
Cheung, C. L. et al., Growth and fabrication with single-walled carbon nanotube probe microscopy tips, Appl. Phys. Lett., 2000, 76: pp. 3136-3138.
Clark, N. A., Smectic-C "chevron," a planar liquid-crystal defect: Implications for the surface-stabilized ferroelectric liquid-crystal geometry, Phys. Rev. A, 1988, 37: pp. 1053-1056.
Costerton, J. W. et al., Bacterial Biofilms: A common cause of persistent infections, Science, 1999, 284: pp. 1318-1322.
Dai et al., "Phase Transformation, Coalescence, an Twinning of Monodisperse FePt Nanocrystals," Nano Letters, vol. 1, No. 8, American Chemical Society, 2001, pp. 443-447.
Dameron et al. :Biosynthesis of Cadmium Sulphide Quantum Semiconductor Crystallites, Letters to Nature, vol. 338, Apr. 13, 1989, pp. 596-597.
Das, P. et al., Liquid crystal polymorphism in F-actin: Optical microscopic and rotatory dispersion studies, J. Chem. Phys., 1999, 111: pp. 8240-8250.
Deschenes, L. et al., Single-molecule studies of heterogeneous dynamics in polymer melts near the glass transition, Science, 2001, 292: pp. 255-258.
Devlin, J. J. et al., Random peptide libraries: A source of specific protein binding molecules, Science, 1990, 249: pp. 404-406.
Devoret, M. H. et al., Amplifying quantum signals with the single-electron transistor, Nature, 2000, 406: pp. 1039-1046.
Dogic, Z. et al., Cholesteric phase in virus suspensions, Langmuir, 2000, 16: pp. 7820-7824.
Dogic, Z. et al., Smectic phase in a colloidal suspension of semiflexible virus particles, Phys. Rev. Lett., 1997, 78: pp. 2417-2420.
Doshi, J. et al., Electrospinning process and applications of electrospun fibers, J. of Electrostatics, 1995, 35: pp. 151-160.
Douglas et al., Host-Guest Encapsulation of Materials by Assembled Virus Protein Cages,: Letters to Nature, vol. 393, Macmilian Publishers, Inc., 1998, pp. 152-155.
Douglas et al., "Nanophase Cobalt Oxyhydroxide Mineral Synthesized Within the Protein Cage of Ferritin," Inorg. Chem., vol. 39, American Chemical Society, 2000, pp. 1828-1830.
Douglas et al., "Synthesis and Structure of an Iron (III) Sulfide-Ferritin Bioinorganic Nanocomposite," Science, vol. 269, Jul. 7, 1995, pp. 54-57.
Douglas, T. et al., Protein engineering of a viral cage for constrained nanomaterials synthesis, Adv. Mater., 2002, 14: pp. 415-418.
Douglas, T. et al., Virus particles as templates for materials synthesis, Adv. Mater., 1999, 11: pp. 679-681.
Duan et al., "Synthesis and optical properties of gallium arsenide nanowires," Applied Physics Letters, vol. 76(9):1116-1118 (2000).
Dujardin et al., "Organization of Metallic Nanoparticles Using Tobacco Mosaic Virus Templates," Nano Letters, vol. 3, No. 3, American Chemical Society, 2002, pp. 413-417.
Falini et al., "Control of Aragonite or Calcite Polymorphism by Mollusk Shell Macromolecules," Science, vol. 271, Jan. 5, 1996, pp. 67-69.
Field, M. et al., Ordering nanometer-scale magnets using bacterial thread templates, Appl. Phys. Lett. 1998, 73: pp. 1739-1741.
Flynn et al., "Synthesis and Organization of Nanoscale II-VI Semiconductor Materials Using Evolved Peptide Specificity and Viral Capsid Assembly," Journal of Materials Chemistry, vol. 13, The Royal Society of Chemistry, 2003, pp. 2414-2421.

Fowler et al., "Tobacco Mosaic Virus Liquid Crystals as Templates for the Interior Design of Silica Mesophases and Nanoparticles," Advanced Materials, vol. 13, No. 16, Wiley-VCH, 2001, pp. 1266-1269.
Fraden, "Phase Transitions in Colloidal Suspensions of Virus Particles"; Baus, M. et al. (ed.), Observation, prediction and simulation of phase transitions in complex fluids, Kluwer Academic Pub., Boston: 1995, pp. 113-164.
Fulton, T. A. et al., Observation of single-electron charging effects in small tunnel junctions, Phys. Rev. Lett., 1987, 59: pp. 109-112.
Glogarova, M., The influence of an external electric field on the structure of chrial sm C* liquid crystal, Mol. Cryst. Liq. Cryst. 1983, 91: pp. 309-325.
Goodby, J. W. et al., A new molecular ordering in helical liquid crystals, J. Am. Chem. Soc., 1989, 111: pp. 8119-8125.
Gray, G.W., et al., "The smectic B phase," Smectic Liquid Crystals—Textures and Structures, pp. 23-44 (Leonard Hill, London, UK 1984).
Haaparanta, T., et al., "A combinatorial method for constructing libraries of long peptides displayed by filamentous phage", Molecular Diversity, pp. 39-52 (1995).
Hartgerink et al., Peptide-Amphiphile Nanofibers: A Versatile Scaffold for the Preparation of Self-Assembling Materials, PNAS, 2002, 99: pp. 5133-5138.
Hayashi, C. et al., Molecular Architecture and Evolution of a Modular Spider Silk Protein Gene, Science, 2000, 287: pp. 1477-1479.
He, S.-J. et al., A twist grain boundary-like twisted smectic phase in monodisperse poly(γ-benzyl α,L-glutamate) produced by recombinant DNA techniques, Macromolecules, 1998, 31: pp. 9387-9389.
Hohman, M. M. et al., Electrospinning and electrically forced jets. I. Stability theory, Physics of Fluids, 2001, 13: pp. 2201-2220.
Hong, S. et al., A Nanoplotter with both parallel and serial writing capabilities, Science, 2000, 288: pp. 1808-1811.
Hong, S. et al., Multiple ink nanolithography: Toward a multiple-pen nano-plotter, Science, 1999, 286: pp. 523-525.
Huang, L. et al., Generation of synthetic elastin-mimetic small diameter fibers and fiber networks, Macromolecules, 2000, 33: pp. 2989-2997.
Issaenko, S.A. et al., Quantum theory of chiral interactions in cholesteric liquid crystals, Phys. Rev. E, 1999, 60: pp. 578-597.
Ito, T. et al., Pushing the limits of lithography, Nature, 2000, 406: pp. 1027-1031.
Jackman, R., Three-dimensional metallic microstructures fabricated by soft lithography and microelectrodeposition, Langmuir, 1999, 15: pp. 826-836.
Jin, H.-J., Electrospinning *Bombyx mori* silk with poly(ethylene oxide), Biomacromolecules, 2002, 3: pp. 1233-1239.
Josephson et al., "High-Efficiency Intracellular Magnetic Labeling with Novel Superparamagnetic-Tat Peptide Conjugates," Bioconjugate Chem., vol. 10, American Chemical Society, 1999, pp. 186-191.
Josephson et al., Bioconjugate Chem., 1999, 10, 186-191.
Jun et al., "Architectural Control of Magnetic Semiconductor Nanocrystals," JACS Articles, vol. 124, No. 4, American Chemical Society, 2002, pp. 615-619.
Kane et al., "Photoreactivity of Platinum (II) in Cisplatin-Modified DNA Affords Specific Cross-Links to HMG Domain Proteins," Biochemistry, vol. 35, American Chemical Society, 1996, pp. 2180-2188.
Kang et al., "Reduction of the fcc to $L1_0$ Ordering Temperature for Self-Assembled FePt Nanoparticles Containing Ag." Nano Letters, vol. 2, No. 10, American Chemical Society, Oct. 2002, pp. 1033-1036.
Kingon, A. I. et al., Alternative dielectrics to silicon dioxide for memory and logic devices, Nature, 2000, 406: pp. 1032-1038.
Kowshik et al., "Microbial Synthesis of Semiconductor PbS Nanocrystallites," Advanced Materials, vol. 14, No. 11, Wiley-VCH, 2002, pp. 815-818.
Labrenz, M. et al, Formation of sphalerite (ZnS) deposits in natural biofilms of sulfate-reducing bacteria, Science, 2000, 290: pp. 1744-1747.

Lapointe, J. et al., Filamentous bacterial viruses VIII. liquid crystals of fd., Mol. Crys. and Liq. Cryst., 1973, 19: pp. 269-278.

Lee et al., "Ordering of Quantum Dots Using Genetically Engineered Viruses," Reports, Science, vol. 296, May 3, 2002, pp. 892-895.

Lee et al., Science, 296, May 3, 2002, 892-895.

Lee, J., et al., "Layer-by-layer growth of CDSE-based nanocrystal light-emitting diodes", Journal of Nanoscience and Nanotechnology, vol. 1, No. 1, pp. 569-664 (2001).

Lee, S.-W. et al., Chiral smectic C structures of virus-based films, Langmuir, 2003, 19: pp. 1592-1598.

Lee, S.-W. et al., Virus-based alignment or inorganic, organic, and biological nanosized materials, Adv. Mat., 2003, 15: pp. 689-692.

Lee, Seung-Wuk, et al., "Ordering of quantum dots using genetically engineered viruses", SCIENCE, vol. 296, pp. 892-895 (May 2002).

Leng Y. et al., Dynamic simulations of adhesion and friction in chemical force microscopy, J. Am. Chem. Soc., 2002, 124: pp. 11764-11770.

Li, D. et al., Electrospinning of polymeric and ceramic nanofibers as uniaxially aligned arrays, Nano Letters, 2003, 3: pp. 1167-1171.

Li, D. et al., Fabrication of titania nanofibers by electrospinning, Nano Letters, 2003, 3: pp. 555-560.

Li, L.-S, et al., Semiconductor nanorod liquid crystals and their assembly on a substrate, Advanced Materials, 2003, 15: pp. 408-411.

Li, L.-S., et al., Semiconductor nanorod liquid crystals, Nano Letters, 2002, 2: pp. 557-560.

Lupinkova et al.,"Histidine Residue 252 of the Photosystem II Di Polypeptide is Involved in a Light Cross-Linking of with the Polypeptide with the α Subunit of Cytochrome b-559: Study of a Site-Directed Mutant of Synechocystis PCC 6803," Biochima et Biophysica Acta, vol. 1554, Elsevier, 2002, pp. 192-201.

Maeda, H., Atomic Force Microscopy Studies for Investigating the Smectic Structures of Colloidal Crystals of β-FeOOH, Langmuir, 1996, 12: pp. 1446-1452.

Maeda, Y. et al., Schiller layers in βferric oxyhydroxide sol as an order-disorder phase separation system, Colloids and Surfaces, 1983, 6: pp. 1-16.

Malik et al., "Role of Capsid Structure and Membrane Protein Processing in Determining the Size and Copy Number of Peptides Displayed on the Major Coat Protein of Filamentous Bacteriophage," J. Med. Biol., vol. 260, Academic Press Limited, 1996, pp. 9-21.

Mann, S. et al., Biologically programmed nanoparticle assembly, Adv. Mater., 2000, 12: pp. 147-150.

Mann, S. et al., Crystalization at inorganic-organic interfaces: biominerals and biomimetic synthesis, Science, 1993, 261: pp. 1286-1292.

Manna et al., "Synthesis of Soluble and Processable Rod-, Arrow-, Teardrop-, and Tetrapod-Shaped CdSe Nanocrystals," J. Am. Chem., vol. 122, American Chemical Society, 2000, pp. 12700-12706.

Mao et al., "Viral Assembly of Oriented Quantum Dot Nanowires," Proc. Nat. Acad. Sci., vol. 100, No. 12, PNAS, 2003, pp. 6946-6951.

Mao et al., "Virus-Based Toolkit for the Directed Synthesis of Magnetic and Semiconducting Nanowires," Reports, vol. 303, Jan. 9, 2004, pp. 213-217.

Mao, Chuanbin, et al., "Viral assembly of oriented quantum dot nanowires", PNAS, vol. 100, No. 12, pp. 6946-6951 (Jun. 2003).

Mathias, J. P., Self-assembly through hydrogen-bonding: peripheral crowding—a new strategy for the preparation of stable supramolecular aggregates based on parallel, connected $CA_3$-$M_3$ rosettes, J. Am. Chem. Soc., 1994, 116: pp. 4326-4340.

Matthews, J. A. et al., Electrospinning of collagen nanofibers, Biomacromolecules 2002, 3: pp. 232-238.

Mattoussi et al., Self-Assembly of CdSe-ZnS Quantum Dot Bioconjugates Using an Engineered Recombinant Protein, J. Am. Chem. Soc., 2000, 122: pp. 12142-12150.

McClelland et al., "Complete Genome Sequence of *Salmonella Enterica* Serovar Typhimurium LT2," Letters to Nature, vol. 413, Macmilian Magazines, Ltd., 2001, pp. 852-856.

Megelski, S. et al., Micro- and nanostructured surface morphology on electrospun polymer fibers, Macromolecules, 2002, 35: pp. 8456-8466.

Meirav, U. et al., Single-electron charging and periodic conductance resonances in GaAs nanostructures, Phys. Rev. Lett., 1990, 65: pp. 771-774.

Melosh, N. A. et al., Ultrahigh-density nanowire lattices and circuits, Science, 2003, 300: pp. 112-115.

Mirkin C. A. et al., A DNA-based method for rationally assembling nanoparticles into macroscopic materials, Nature, 1996, 382: pp. 607-609.

Mooney et al., "Histidine Modifying Agents Abolish Pyruvate Dehydrogenase Kinase Activity," Biochemical and Biophysical Research Communications, vol. 267, Academic Press, 2000, pp. 500-503.

Mukherjee et al., "Fungus-Mediated Synthesis of Ag Nanoparticles and their Immobilization in the Mycelial Matrix: A Novel Biological Approach to Nanoparticle Synthesis," Nano Letters, vol. 1, No. 10, American Chemical Society, 2001, pp. 515-519.

Muthukumar, M. et al., Competing interactions and levels of ordering in self-organizing polymeric materials, Science, 1997, 277: pp. 1225-1232.

Naik et al., "Biomimetric Synthesis and Patterning of Silver Nanoparticles," Nature Material, vol. 1, Nature Publishing Group, 2002, pp. 169-172.

Naik et al., "Silica-Precipitating Peptides Isolated From A Combinatorial Phage Display Peptide Library," Journal of Nanoscience and Nanotechnology, vol. 2, No. 1, American Scientific Publishers, 2002, pp. 95-100.

Naik, R., et al., "Biomimetic synthesis and patterning of silver nanoparticles," Nature Materials, vol. 1, No. 3, pp. 169-172 (Nov. 2002).

Niikura, K., Ordering of Inorganic Nanocrystals Using Viruses Kagaku to Kogyo (Tokyo, Japan) vol., 55, No. 2, p. 1363 (2002).

Norris, D. J. et al., Size dependence of exciton fine structure in CdSe quantum dots, Phys. Rev. B, 1996, 53: pp. 16347-16354.

Nygaard, S. et al., Surface-specific zeolite-binding proteins, Adv. Mat., 2002, 14: pp. 1853-1856.

Onsager, L., The effects of shape on the interaction of colloidal particles, Annals N.Y. Acad. Sci., 1949, 51: p. 627-659.

Parge et al., "Structure of the Fibre-Forming Protein Pilin at 2.6 A Resolution," Articles, Nature, vol. 378, Nov. 1995, pp. 32-38.

Patrick D. L. et al., Atomistic molecular dynamics simulations of chemical force microscopy, J. Am. Chen. Soc., 2003, 125: pp. 6762-6773.

Patrick, D. L. et al., Nanometer-scale aspects of molecular ordering in nanocrystalline domains at a solid interface: The role of liquid crystal-surface interactions studied by STM and molecule corrals, J. of Phys. Chem. B., 1999, 103: pp. 8328-8336.

Peercy, P. S., The drive to miniaturization, Nature, 2000, 406: pp. 1023-1026.

Percec, V. et al., Self-organization of supramolecular helical dendrimers into complex electronic materials, Nature, 2002, 419, pp. 384-387, 862.

Perez et al., "Viral-Induced Self-Assembly of Magnetic Nanoparticles Allowas the Detection of Viral Particles in Biological Media," J. Am. Chem. Soc., vol. 125, American Chemical Society, 2003, pp. 10192-10193.

Puntes et al., "Colloidal Nanocrystal Shape and Size Control: The Case of Cobalt," Reports, Science, vol. 291, Mar. 16, 2001, pp. 2115-2117.

Qin, D. et al., Fabrication of ordered two-dimensional arrays of micro- and nanoparticles using patterned self-assembled monolayers as templates, Adv. Mater., 1999, 11: pp. 1433-1437.

Reiss, Brian D., et al., "Biological Routes to Metal Alloy Ferromagnetic Nanostructures", Nano. Lett. pp. A-F (2004).

Reynolds, T. et al., Bakers' yeast, a model for fungal biofilm formation, Science, 2001, 291: pp. 878-881.

Roth, T. A. et al., A minimized M13 coat protein defines the requirements for assembly into the bacteriophage particle, J. Mol. Biol., 2002, 322: pp. 357-367.

Rueckes, T. et al., Carbon nanotube-based nonvolatile random access memory for molecular computing, Science, 2000, 289: pp. 94-97.

Sakaguchi et al., "Magnetite Formation by a Sulphate-Reducing Bacterium," Letters to Nature, vol. 365, Sep. 2, 1993, pp. 47-49.

Schoelkopf, R. J. et al., The radio-frequency single-electron transistor (RF-SET): A fast and ultrasensitive electrometer, Science, 1998, 280: pp. 1238-1242.

Seeman, N. C. et al., Emulating biology: Building nanostructures from the bottom up, Proc. Natl. Acad. Sci., 2002, 99: pp. 6451-6455.

Seeman, N. C., DNA in a material world, Nature, 2003, 421: pp. 427-431.

Shenton et al., "Synthesis of Nanophase Iron Oxide in Lumazine Synthase Capsids," Angew. Chem. Int. Ed., vol. 40, No. 2, Wiley-VCH, 2001, pp. 442-445.

Shenton, W. et al., Synthesis of cadmium sulphide superlattices using self-assembled bacterial S-layers, Nature, 1997, 389: pp. 585-587.

Sonin, A.A., Freely Suspended Liquid Crystalline Films, (John Wiley & Sons, Ltd, New York, 1998), pp. 25-43.

Su et al., "Structural and Microstructural Characterization of the Growth Lines and Prismatic Microarchetecture in Red Abalone Shell and the Microstructures of Abalone Flat Pearls," Chem. Mater., vol. 14, American Chemical Society, 2002, pp. 3106-3117.

Sun et al., "Monodisperse FePt Nanoparticles and Ferromagnetic FePt Nanocrystal Superlattices," Reports, Science, vol. 287, Mar. 17, 2000, pp. 1989-1992.

Taylor, G., Electrically driven jets, Proc. Roy. Soc. Lond. A., 1969, 313: pp. 453-475.

Tsortos, A. et al., The dual role of fibrinogen as inhibitor and nucleator of calcium phosphate phases: The importance of structure, J. of Colloid and Interface Science, 1996, 177: pp. 257-262.

Valluzzi, R. et al., Silk: molecular organization and control of assembly, Phil. Trans. R. Soc. Lond. B., 2002, 357: pp. 165-167.

Vollrath, F. et al., Liquid crystalline spinning of spider silk, Nature, 2001, 410: pp. 541-548.

Walba, D. M. et al., Detecting molecular chirality by scanning tunneling microscopy, Acc. Chem. Res., 1996, 29: pp. 591-597.

Wang, X. et al., Electrospun nanofibrous membranes for highly sensitive optical sensors, Nano Letters, 2002, 2: pp. 1273-1275.

Warne et al., Self Assembled Nanoparticulate Co:Pt for Data Storage Applications, IEEE Transactions on Magnetics, vol. 36, No. 5, Sep. 2000, pp. 3009-3011.

Weber, P. C. et al., Structural origins of high-affinity biotin binding to streptavidin, Science, 1989, 243: pp. 85-88.

Welsh, L. C. et al., Evidence for tilted smectic liquid crystalline packing of fd *Inovirus* from x-ray fiber diffraction, Macromolecules, 1996, 29: pp. 7075-7083.

Whaley et al., "Selection of Peptides with Semiconductor Binding Specificity for Directed Nanocrystal Assembly," Letters to Nature, vol. 405, Macmilian Magazines, Ltd., Jun. 2000, pp. 665-668.

Whaley, S. R., "Borrowing Ideas from Nature: Peptide specific to gallium arsenide", Materials Research Soc. Symposium Proceedings, vol. 599, pp. 189-199 (2000).

Whitchurch, C. B. et al., Extracellular DNA required for bacterial biofilm formation, Science, 2002, 295: p. 1487.

Wnek, G. E. et al., Electrospinning of nanofiber fibrinogen structures, Nano Letters, 2003, 3: pp. 213-216.

Wong et al., "Biomimetric Synthesis of Cadmium Sulfide-Ferritin Nanocomposites," Adv. Mater., vol. 8, 1996, pp. 928-932.

Yao, Z. et al., Carbon nanotube intramolecular junctions, Nature, 1999, 402: pp. 273-276.

Yu, S. M. et al., Smectic ordering in solutions and films of a rod-like polymer owing to monodispersity of chain length, Nature, 1997, 389: pp. 167-170.

Zaremba et al., "Critical Transitions in the Biofabrication of Abalone Shells and Flat Pearls," Chem. Mater., vol. 8, American Chemical Society, 1996, pp. 679-690.

Zheng, W. Y. et al., Mesogen orientation with smectic C* side chain liquid crystalline diblock copolymers, Macromolecules, 1998, 31: pp. 2686-2689.

FIG. 3A    FIG. 3B    FIG. 3C
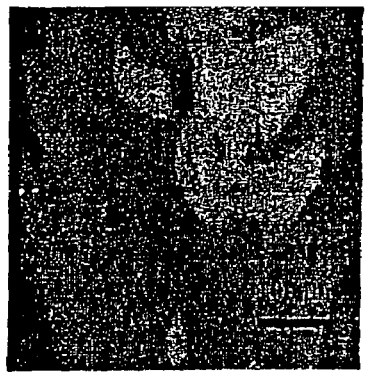 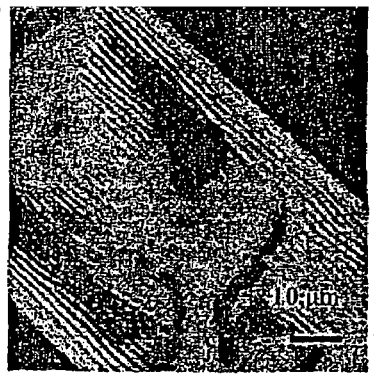 
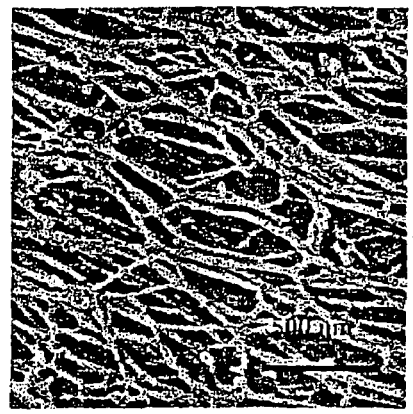 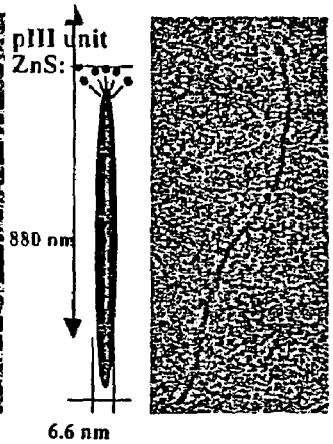 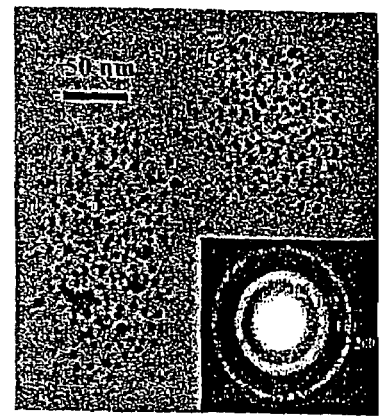
FIG. 3D    FIG. 3E  FIG. 3F    FIG. 3G FIG. 5A
FIG. 5B
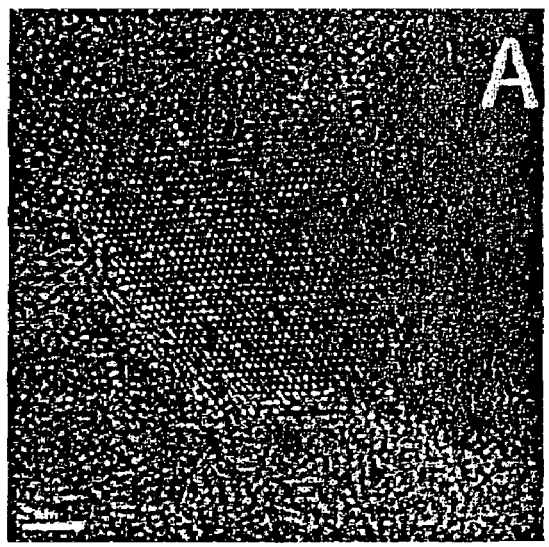
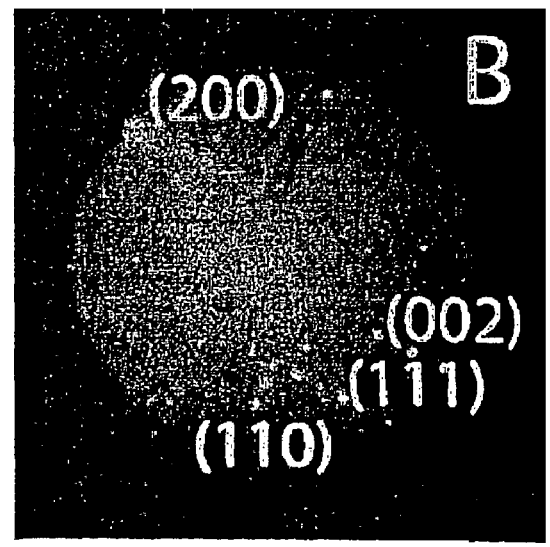
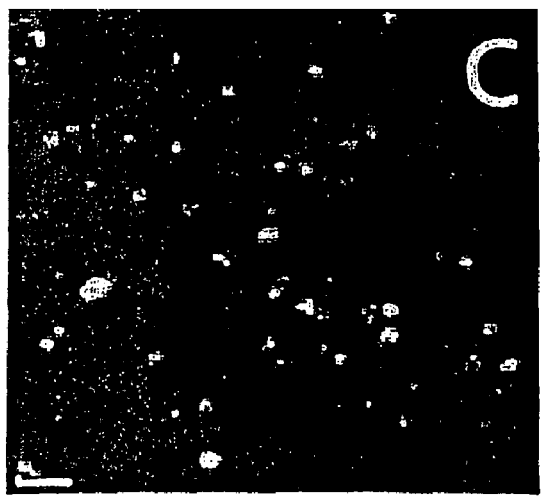
FIG. 5C

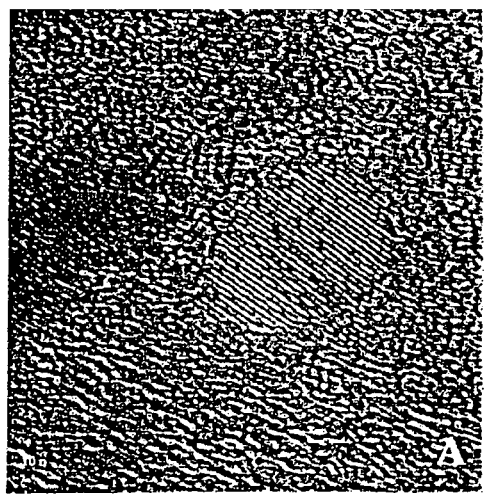 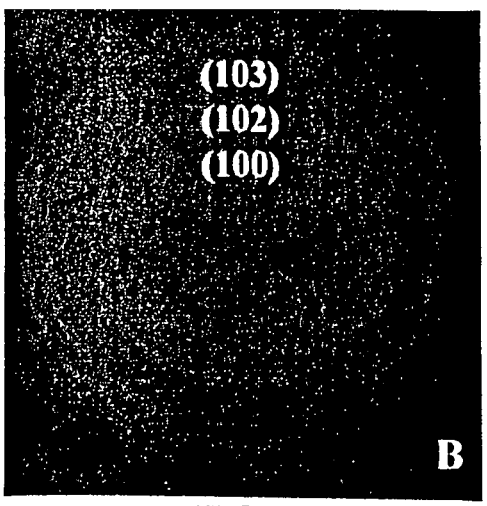
FIG. 8A FIG. 8B

FIG. 14A
FIG. 14B
FIG. 14C
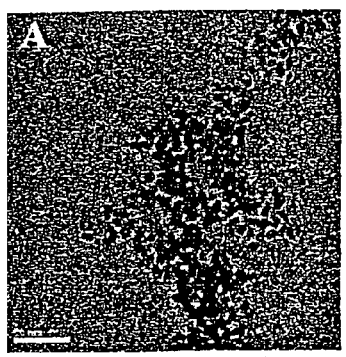
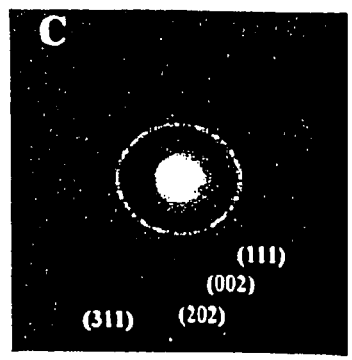
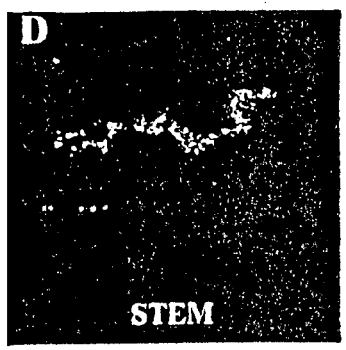
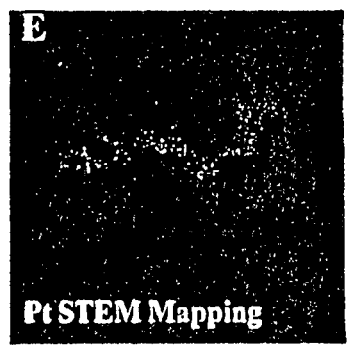
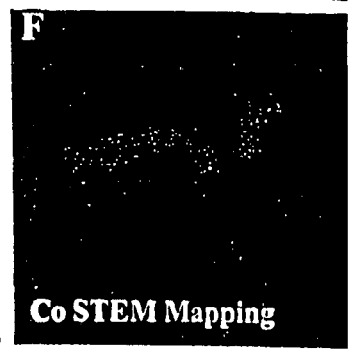
FIG. 14D
FIG. 14E
FIG. 14F

SEQUENCE LISTING

```
<160> NUMBER OF SEQ ID NOS: 18

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ala Met Ala Gly Thr Thr Ser Asp Pro Ser Thr Val
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 2

Pro Ala Gln Ser Met Ser Gln Thr Pro Ser Ala Ala
 1               5                  10

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

His Thr His Thr Asn Asn Asp Ser Pro Asn Gln Ala
 1               5                  10

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Asp Thr Gln Gly Phe His Ser Arg Ser Ser Ser Ala
 1               5                  10

<210> SEQ ID NO 5
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Thr Ser Ser Ser Ala Leu Gln Pro Ala His Ala Trp
 1               5                  10

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ser Glu Ser Ser Pro Ile Ser Leu Asp Tyr Arg Ala
 1               5                  10

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ser Thr His Asn Tyr Gln Ile Pro Arg Pro Pro Thr
 1               5                  10

<210> SEQ ID NO 8
<211> LENGTH: 12
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 8

His Pro Phe Ser Asn Glu Pro Leu Gln Leu Ser Ser
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ser Ser Leu Phe Ile Gln Gln Asn Ala Leu Thr Gly
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Pro Phe Pro Thr Met Pro Leu Pro Asn Gly His
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Ser Gly Gln Leu Pro Ile Ala Leu Glu Leu Arg
1               5                   10

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Asn Ala Gly Asp His Ala Asn
1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ser Lys Asn Ser Asn Ile Leu
1               5
```

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Thr Lys Pro Ser Val Val Gln
1               5

<210> SEQ ID NO 15
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ala Leu Ser Pro His Ser Ala Pro Leu Thr Leu Tyr
1               5                   10

<210> SEQ ID NO 16
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ser Val Ser Val Gly Met Lys Pro Ser Pro Arg Pro
1               5                   10

<210> SEQ ID NO 17
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

His Asn Lys His Leu Pro Ser Thr Gln Pro Leu Ala
1               5                   10

<210> SEQ ID NO 18
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Trp Asp Pro Tyr Ser His Leu Leu Gln His Pro Gln
1               5                   10

US 7,374,893 B2

PEPTIDE MEDIATED SYNTHESIS OF METALLIC AND MAGNETIC MATERIALS

RELATED APPLICATIONS

This application is a continuation of application Ser. No. 10/665,721, filed Sep. 22, 2003, which claims benefit of provisional patent application Ser. No. 60/411,804, filed Sep. 18, 2002, to Belcher et al., both of which are hereby incorporated by reference in their entirety.

STATEMENT OF GOVERNMENT SUPPORT

The research carried out in the subject application was supported in part by grants from the Army Research Office, Grant No. DADD19-99-0155, the government may own certain rights.

In addition, a nucleotide and/or amino acid sequence listing is incorporated by reference of the material on computer readable form.

TECHNICAL FIELD OF THE INVENTION

The present invention is directed to organic materials capable of binding to inorganic materials, and specifically, toward specific peptide sequences that tightly and directly bind to metal materials including magnetic materials.

BACKGROUND OF THE INVENTION

In biological systems, organic molecules exert a remarkable level of control over the nucleation and mineral phase of inorganic materials such as calcium carbonate and silica, and over the assembly of building blocks into complex structures required for biological function.

Materials produced by biological processes are typically soft, and consist of a surprisingly simple collection of molecular building blocks (i.e., lipids, peptides, and nucleic acids) arranged in astoundingly complex architectures. Unlike the semiconductor industry, which relies on a serial lithographic processing approach for constructing the smallest features on an integrated circuit, living organisms execute their architectural "blueprints" using mostly non-covalent forces acting simultaneously upon many molecular components. Furthermore, these structures can often elegantly rearrange between two or more usable forms without changing any of the molecular constituents.

The use of "biological" materials to process the next generation of microelectronic devices provides a possible solution to resolving the limitations of traditional processing methods. The critical factors in this approach are identifying the appropriate compatibilities and combinations of biological-inorganic materials, and the synthesis of the appropriate building blocks.

SUMMARY OF THE INVENTION

The present inventors have designed constructs and produced biological materials that direct and control the assembly of inorganic materials, including metallic and magnetic materials, into controlled and sophisticated structures. Of particular interest are ferromagnetic materials, and particulate materials including nanoparticulate materials. The use of biological materials to create and design materials that have interesting electrical, magnetic or optical properties may be used to decrease the size of features and improve the control of, e.g., the opto-electical properties of the material, as well as control of material fabrication. For example, room temperature methods have been developed in the present invention for preparing materials which formerly involved high temperature preparation methods.

A combinatorial peptide phage display library expressing a large collection of bacterial phage that expresses millions of different peptide sequences on their surfaces was combined with biopanning techniques to select specific peptide sequences that tightly and directly bind to metal materials including magnetic materials (e.g., Co, CoPt SmCo5, or FePt). The present inventors have found that these metal and magnetic material binding molecules, including peptides, can be used to control the nucleation of inorganic materials, as has been demonstrated in nature and with II-VI semiconductors. If proteins can be used to control the nucleation of metal, including magnetic, materials, then magnetic nanoparticles and their applications could be prepared much cheaper and easier than using traditional methods. The nanomolecular metals, including magnets and magnetic material, may be used, e.g., for micro or nanomachines, dynamos, generators, magnetic storage or any other applications for materials that are magnetic or may be magnetized. Another use for these materials is to modify the surface of metal, including magnetic, materials. The peptides can act as linkers for attaching over materials to the surface of the magnetic material, allowing the self-assembly of complex nanostructures, which could form the basis of novel electronic devices.

The present inventors have recognized that this approach of selecting binding peptides (using combinatorial peptide libraries and panning techniques) may also be used to form and control the nucleation of metal materials, including magnetic materials. Other techniques being researched to synthesize metal particles, including magnetic nanoparticles, are based on a high temperature synthesis that must be performed in an inert atmosphere using expensive reagents and often require further processing and purification after synthesis to fabricate particles, including nanoparticles, with the desired shape and crystallinity. The result is that preparing magnetic nanoparticles in the traditional fashion is expensive and not conducive to large scale and/or volume production. The approach presented herein is generally performed at room temperatures using inexpensive reagents yielding nanoparticles with controlled crystallinity, reducing the cost for the synthesis of metal particles, including magnetic nanoparticles, with controlled crystal structure and orientation.

Peptide-mediated synthesis of metal materials, including magnetic materials, provides a much cheaper and environmentally friendly approach to the synthesis of metal materials, including magnetic nanoparticles. Current protocols for preparing metal nanoparticles, including magnetic nanoparticles, are time consuming, expensive and yield nanoparticles coated with organic surfactants. These surfactants are not amicable to further modification of the nanoparticles. Advances in the field of molecular biology enable the functionalization of peptides, therefore, particles and nanoparticles grown from peptides will also be easily functionalized. Peptide functionalization facilitates their incorporation into electronic devices and integration into magnetic memory devices.

One form of the present invention is a method for using self-assembling biological molecules, e.g., bacteriophage, that are genetically engineered to bind to metals, nanoparticles-, and magnetic or other materials and to organize well-ordered structures. These structures may be, e.g., nanoscale arrays of particles and nanoparticles. Using bacteriophage as an example, self-assembling biological materials can be selected for specific binding properties to particular surfaces (e.g., semiconductor), and thus, the modified bacteriophage and the methods taught herein may be used to create well-ordered structures of the materials selected.

More particularly, the present invention includes compositions and methods for creating metal materials, including magnetic materials, particles, and nanoparticles. One embodiment is a method of making a metal particle, including magnetic particle, including the steps of; providing a molecule comprising a portion that binds specifically to a metal surface, including a magnetic surface, and contacting one or more metal material precurosrs, including magnetic material precursors, with the molecule under conditions that permit formation of the metal material, including the magnetic particle. The molecule may be, e.g., a biological molecule such as an amino acid oligomer or peptide. The oligomer may be, for example, between about 7 and about 100 amino acids long, and more particularly, between about 7 and about 30 amino acids long, and more particularly about 7 and about 20 amino acids long, and may form part of a combinatorial library and/or include a chimeric molecule.

The types of metal materials, including magnetic particles, that are disclosed herein may be formed from, e.g., Co, CoPt, SmCo5, and/or FePt. Another method of the present invention includes a method for identifying molecules that bind through non-magnetic interactions with a magnetic material including the steps of contacting an amino acid oligomer library with a magnetic material to select oligomers that bind specifically to the magnetic material and eluting those oligomers that bind specifically to the magnetic material. The oligomer library may be a library of self-assembling molecules, e.g., a phage library such as an M13 phage library. The library may even be contained in a bacterium and may be assembled externally.

A method of making a magnetic particle may also include the step of contacting a molecule that initiates magnetic molecule formation with magnetic material precursors and a reducing agent. The molecule that initiates magnetic molecule formation with magnetic material precursors may be contacted at, e.g., room temperature or below a temperature of, e.g., 100, 200 or even 300 degrees centigrade. The molecule may be an amino acid oligomer of, e.g., between about 7 and 20 amino acids long. The magnetic particle may be a Co, CoPt, SmCo5, or FePt magnetic particle in the form of a magnetic quantum dot or even a film. The skilled artisan will recognize that combinations or one or more of the magnetic particles disclosed herein may be positioned in a wide assortment of one-, two- and three-dimensional locations, shapes, and the like for particular uses.

The present invention also includes magnetic particles, e.g., nanoparticles made by the methods disclosed herein. These magnetic particles may form a portion of an integrated circuit made by fixing a magnetic material binding peptide to a substrate; contacting one or more magnetic material precursors with the magnetic material binding peptide under conditions that form a magnetic particle; and forming a magnetic crystal on the substrate. The magnetic material binding peptide may be linked chemically to a substrate, e.g., silicon or other semiconductor substrate. The magnetic particles of the present invention may be used to make memory, short- or long-term storage, identification systems or any use that the skilled artisan will recognize may be made of these particles. Examples of other used for the magnetic micro-, nano- and femto-particles of the present invention include, micro or nano-motors, dynamos and the like.

Another form of the present invention is a method of creating nanoparticles that have specific alignment properties. This is accomplished by creating, e.g., an M13 bacteriophage that has specific binding properties, amplifying the bacteriophage to high concentrations (e.g., incubation of phage library with bacterial host culture to allow infection, replication, and subsequent purification of virus), and resuspending the phage.

This same method may be used to create bacteriophage that have three liquid crystalline phases, a directional order in the nemetic phase, a twisted nemetic structure in the cholesteric phase, and both directional and positional order in smectic phase. In one aspect the present invention is a method of making a polymer, e.g., a film, comprising the steps of, amplifying a self-assembling biological molecule comprising a portion that binds a specific semiconductor surfaces to high concentrations and contacting one or more semiconductor material precursors with the self-assembling biological molecule to form or direct the formation of a crystal.

Another form of the present invention is method for creating nanoparticles that have differing cholesteric pitches by using, e.g., an M13 bacteriophage that has been selected to bind to semiconductor surfaces and resuspending the phage to various concentrations. Another form of the present invention is a method of preparing a casting film with aligned nanoparticles by using, e.g., genetically engineered M13 bacteriophage and re suspending the bacteriophage.

Still another form of the present invention is a method of preparing a nanoparticle film comprising the steps of adding a solution of nanoparticles to a surface, evaporating the solution of nanoparticles on the surface, and annealing the nanoparticles to the surface, where the nanoparticles are magnetic molecules. The surface may include any microfabricated solid surface to which molecules may attach through either covalent or non-covalent bonds, such Langmuir-Bodgett films, glass, functionalized glass, germanium, silicon, PTFE, polystyrene, gallium arsenide, gold, silver, or any materials comprising amino, carboxyl, thiol or hydroxyl functional groups incorporated onto a surface. Annealing generally occurs by high temperatures under an inert gas (e.g., nitrogen). Another form of the present invention is a nanoparticle film prepared by the method just described.

BRIEF DESCRIPTION OF THE FIGURES

For a more complete understanding of the features and advantages of the present invention, reference is now made to the detailed description of the invention along with the accompanying FIGURES in which corresponding numerals in the different FIGURES refer to corresponding parts and in which:

FIG. 3 include images of the A7-ZnS suspensions using (A-B) POM, (C) AFM, (D) SEM, (E) TEM, and (FG) TEM image with electron diffraction insert;

FIG. 5 is (A) TEM image of annealed SmCo5 nanoparticles, (B) TEM image with the selected area electron diffraction pattern and (C) STEM image of annealed SmCo5 nanoparticles;

FIG. 8 is (A) high resolution TEM image of Co nanoparticles that have been grown using a 12mer peptide that selectively bind to Co and (B) the corresponding electron diffraction pattern;

FIG. 14 include (A) TEM of CoPt nanoparticles grown using a phage that has been genetically engineered to express a CoPt specific 12mer sequence on their P8 proteins, (B) higher resolution TEM image of the same CoPt nanoparticles, (C) the corresponding electron diffraction pattern, (D) STEM image of similarly prepared particles, (E) STEM mapping for Pt, and (F) STEM mapping for Co in accordance with the present invention.

DETAILED DESCRIPTION OF THE INVENTION

Figure 1A:
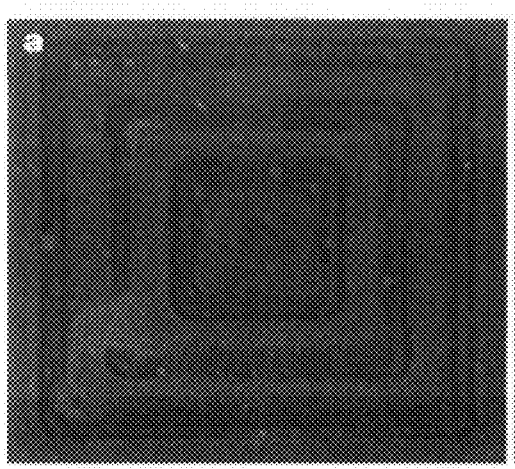
FIG. 1 are X-ray photoelectron spectroscopy (XPS) elemental composition determination of phage-substrate interactions through the intensity of a gold 4f-electron signal (A-C), model of phage discrimination for semiconductor heterostructures (D), and examples of bivalent synthetic peptides with two-component recognition attachments (E-F)

This application claims benefit of provisional patent application Ser. No. 60/411,804 filed Sep. 18, 2002 to Belcher et al., which is hereby incorporated by reference in its entirety including the figures, summary, detailed description, working examples, claims, and sequence listing.

Although making and using various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention, and do not delimit the scope of the invention.

To facilitate the understanding of this invention, a number of terms are described further below. As used herein, "metal material" can be, for example, a substance that encompasses, but is not limited to, metal alloys, metal oxides, and pure metals, that may or may not have the magnetic and/or ferromagnetic properties, may be crystalline, polycrystalline or amorphous. Metal materials may also exist in several spatial forms, including particles, patterned surfaces or layered films. The term "particle" can refer to the size and shape of said materials, and includes but is not limited to micron-scaled particles, nano-scaled particles (called nanoparticles), single molecule of metal materials and other sizes and shapes here unsaid but controlled by the described biological methods.

The term binding molecule is hereby defined as a molecule that binds, recognizes or directs the growth of a metal material. Examples of binding molecules includes but are not limited to peptides, amino acid oligomers, and nucleic acid oligomers. These binding molecules may be selected from combinatorial library screening, or synthesized, conjugated or formulated independently from such libraries. These binding molecules may be coupled to a substrate, i.e. conjugated to a surface or to scaffolds, such as M13 viruses where the binding molecules are displayed on viral coats or various binding molecule-conjugated structures.

The inventors have previously shown that peptides can bind to semiconductor materials. In the present invention, the inventors demonstrate that binding molecules, including peptides, can specifically bind to metal materials, including magnetic materials. These peptides have been further developed into a way of nucleating nanoparticles and directing their self-assembly. The main features of the peptides are their ability to recognize and bind technologically important materials with face specificity, to nucleate size-constrained crystalline semiconductor materials, and to control the crystallographic phase of nucleated nanoparticles. The peptides can also control the aspect ratio of the nanoparticles and therefore, the optical properties.

Briefly, the facility with which biological systems assemble immensely complicated structure on an exceedingly minute scale has motivated a great deal of interest in the desire to identify non-biological systems that can behave in a similar fashion. Of particular value would be methods that could be applied to materials with interesting electronic or optical properties, but of which natural evolution has not selected for interactions between biomolecules and such materials.

The present invention is based on recognition that biological systems efficiently and accurately assemble nanoscale building blocks into complex and functionally sophisticated structures with high perfection, controlled size and compositional uniformity.

Peptide Sequence Selection

One method of providing a random organic polymer pool is using a Phage-display library, based on a combinatorial library of random peptides containing between 7 and 12 amino acids fused to the pIII coat protein of M13 bacteriophage, providing different peptides that were reacted with crystalline semiconductor structures. Five copies of the pIII coat protein are located on one end of the phage particle, accounting for 10-16 nm of the particle. The phage-display approach provided a physical linkage between the peptide substrate interaction and the DNA that encodes that interaction. The examples described here used as examples, five different single-crystal semiconductors: GaAs (100), GaAs (111)A, GaAs(111)B, InP(100) and Si(100). These substrates allowed for systematic evaluation of the peptide substrate interactions and confirmation of the general utility of the methodology of the present invention for different crystalline structures.

Protein sequences that successfully bound to the specific crystal were eluted from the surface, amplified by, e.g., a million-fold, and reacted against the substrate under more stringent conditions. This procedure was repeated five times to select the phage in the library with the most specific binding. After, e.g., the third, fourth and fifth rounds of phage selection, crystal-specific phage were isolated and their DNA sequenced. Peptide binding has been identified that is selective for the crystal composition (for example, binding to GaAs but not to Si) and crystalline face (for example, binding to (100) GaAs, but not to (111)B GaAs).

Twenty clones selected from GaAs(100) were analyzed to determine epitope binding domains to the GaAs surface. The partial peptide sequences of the modified pIII or pVIII protein are shown in TABLE 1, revealing similar amino-acid sequences among peptides exposed to GaAs.

TABLE 1

Partial peptide sequences of modified pIII or pVIII proteins.

| | | |
|---|---|---|
| G13-5 | AMAGTTSDPSTV | SEQ ID NO.: 1 |
| G12-5 | PAQSMSQTPSAA | SEQ ID NO.: 2 |
| G12-3 | HTHTNNDSPNQA | SEQ ID NO.: 3 |
| G1-4 | DTQGFHSRSSSA | SEQ ID NO.: 4 |
| G12-4 | TSSSALQPAHAW | SEQ ID NO.: 5 |
| G14-3 | SESSPISLDYRA | SEQ ID NO.: 6 |
| G7-4 | STHNYQIPRPPT | SEQ ID NO.: 7 |
| G15-5 | HPFSNEPLQLSS | SEQ ID NO.: 8 |
| G14-4 | SSLFIQQNALTG | SEQ ID NO.: 9 |
| G11-3 | GPPPTMPLPNGH | SEQ ID NO.: 10 |
| G1-3 | GSGQLPIALELR | SEQ ID NO.: 11 |

With increasing number of exposures to a GaAs surface, the number of uncharged polar and Lewis-base functional groups increased. Phage clones from third, fourth and fifth round sequencing contained on average 30%, 40% and 44% polar functional groups, respectively, while the fraction of Lewis-base functional groups increased at the same time from 41% to 48% to 55%. The observed increase in Lewis bases, which should constitute only 34% of the functional groups in random 12-mer peptides from our library, suggests that interactions between Lewis bases on the peptides and Lewis-acid sites on the GaAs surface may mediate the selective binding exhibited by these clones.

The expected structure of the modified 12-mers selected from the library may be an extended conformation, which seems likely for small peptides, making the peptide much longer than the unit cell (5.65 A°) of GaAs. Therefore, only small binding domains would be necessary for the peptide to recognize a GaAs crystal. These short peptide domains, highlighted in TABLE 1, contain serine- and threonine-rich regions in addition to the presence of amine Lewis bases, such as asparagine and glutamine. To determine the exact binding sequence, the surfaces have been screened with shorter libraries, including 7-mer and disulphide constrained 7-mer libraries. Using these shorter libraries that reduce the size and flexibility of the binding domain, fewer peptide-surface interactions are allowed, yielding the expected increase in the strength of interactions between generations of selection.

Figure 1B:
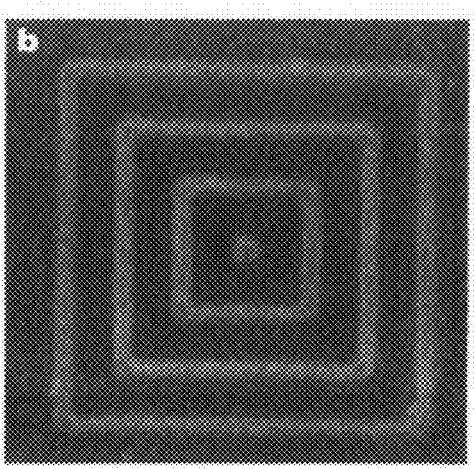
Figure 1C:
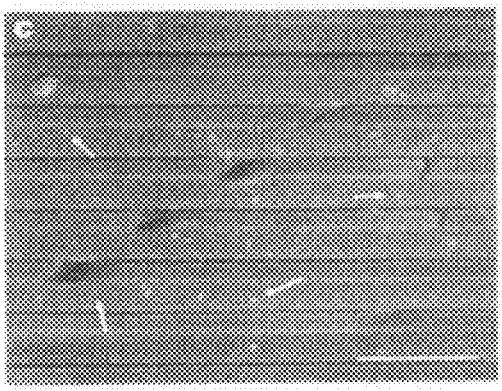

Phage, tagged with streptavidin-labeled 20-nm colloidal gold particles bound to the phage through a biotinylated antibody to the M13 coat protein, were used for quantitative assessment of specific binding. X-ray photoelectron spectroscopy (XPS) elemental composition determination was performed, monitoring the phage substrate interaction through the intensity of the gold 4f-electron signal (FIGS. 1A-C). Without the presence of the G1-3 phage, the antibody and the gold streptavidin did not bind to the GaAs(100) substrate. The gold-streptavidin binding was, therefore, specific to the phage and an indicator of the phage binding to the substrate. Using XPS it was also found that the G1-3 clone isolated from GaAs(100) bound specifically to GaAs(100) but not to Si(100) (see FIG. 1A). In complementary fashion the Si clone, screened against the (100) Si surface, showed poor binding to the (100) GaAs surface.

Some GaAs clones also bound the surface of InP (100), another zinc-blende structure. The basis of the selective binding, whether it is chemical, structural or electronic, is still under investigation. In addition, the presence of native oxide on the substrate surface may alter the selectivity of peptide binding.

The preferential specific binding of the G1-3 clone to GaAs(100), over the (111)A (gallium terminated) or (111)B (arsenic terminated) face of GaAs was demonstrated (FIG. 1B, C). The G1-3 clone surface concentration was greater on the (100) surface, which was used for its selection, than on the gallium-rich (111)A or arsenic-rich (111)B surfaces. These different surfaces are known to exhibit different chemical reactivities, and it is not surprising that there is selectivity demonstrated in the phage binding to the various crystal faces. Although the bulk termination of both 111 surfaces give the same geometric structure, the differences between having Ga or As atoms outermost in the surface bilayer become more apparent when comparing surface reconstructions. The composition of the oxides of the various GaAs surfaces is also expected to be different, and this in turn may affect the nature of the peptide binding.

The intensity of Ga 2p electrons against the binding energy from substrates that were exposed to the G1-3 phage clone is plotted in FIG. 1C. As expected from the results in FIG. 1B, the Ga 2p intensities observed on the GaAs (100), (111)A and (111)B surfaces are inversely proportional to the gold concentrations. The decrease in Ga 2p intensity on surfaces with higher gold-streptavidin concentrations was due to the increase in surface coverage by the phage. XPS is a surface technique with a sampling depth of approximately 30 angstroms; therefore, as the thickness of the organic layer increases, the signal from the inorganic substrate decreases. This observation was used to confirm that the intensity of gold-streptavidin was indeed due to the presence of phage containing a crystal specific bonding sequence on the surface of GaAs. Binding studies were performed that correlate with the XPS data, where equal numbers of specific phage clones were exposed to various semiconductor substrates with equal surface areas. Wild-type clones (no random peptide insert) did not bind to GaAs (no plaques were detected). For the G1-3 clone, the eluted phage population was 12 times greater from GaAs(100) than from the GaAs(111)A surface.

The G1-3, G12-3 and G7-4 clones bound to GaAs(100) and InP(100) were imaged using atomic force microscopy (AFM). The InP crystal has a zinc-blende structure, isostructural with GaAs, although the In—P bond has greater ionic character than the GaAs bond. The 10-nm width and 900-nm length of the observed phage in AFM matches the dimensions of the M13 phage observed by transmission electron microscopy (TEM), and the gold spheres bound to M13 antibodies were observed bound to the phage (data not shown). The InP surface has a high concentration of phage. These data suggest that many factors are involved in substrate recognition, including atom size, charge, polarity and crystal structure.

Figure 1D:
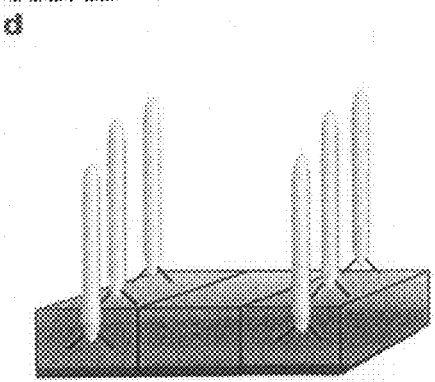
Figure 1E:
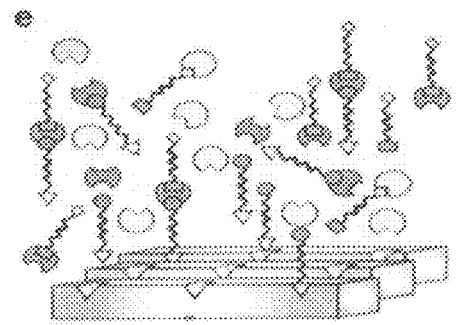

The G1-3 clone (negatively stained) is seen bound to a GaAs crystalline wafer in the TEM image (not shown). The data confirms that binding was directed by the modified pIII protein of G1-3, not through non-specific interactions with the major coat protein. Therefore, peptides of the present invention may be used to direct specific peptide-semiconductor interactions in assembling nanostructures and heterostructures (FIG. 1E).

X-ray fluorescence microscopy was used to demonstrate the preferential attachment of phage to a zinc-blende surface in close proximity to a surface of differing chemical and structural composition. A nested square pattern was etched into a GaAs wafer; this pattern contained 1-μm lines of GaAs, and 4-μm $SiO_2$ spacing in between each line (FIGS. 1A-1B). The G12-3 clones were interacted with the GaAs/$SiO_2$ patterned substrate, washed to reduce non-specific binding, and tagged with an immuno-fluorescent probe, tetramethyl rhodamine (TMR). The tagged phage were found as the three lighter lines (red, if in color) and the center dot, in FIG. 1B, corresponding to G12-3 binding only to GaAs. The $SiO_2$ regions of the pattern remain unbound by phage and are dark in color. This result was not observed on a control that was not exposed to phage, but was exposed to the primary antibody and TMR (FIG. 1A). The same result was obtained using non-phage bound G12-3 peptide.

The GaAs clone G12-3 was observed to be substrate-specific for GaAs over AlGaAs (FIG. 1C). AlAs and GaAs have essentially identical lattice constraints at room temperature, 5.66 A° and 5.65 A°, respectively, and thus ternary alloys of AlxGa1-xAs can be epitaxially grown on GaAs substrates. GaAs and AlGaAs have zinc-blende crystal structures, but the G12-3 clone exhibited selectivity in binding only to GaAs. A multilayer substrate was used, consisting of alternating layers of GaAs and of $Al_{0.98}Ga_{0.02}As$. The substrate material was cleaved and subsequently reacted with the G12-3 clone.

The G12-3 clones were labeled with 20-nm gold-streptavidin nanoparticles. Examination by scanning electron microscopy (SEM) shows the alternating layers of GaAs and $Al_{0.98}Ga_{0.02}As$ within the heterostructure (FIG. 1C). X-ray elemental analysis of gallium and aluminum was used to map the gold-streptavidin particles exclusively to the GaAs layers of the heterostructure, demonstrating the high degree of binding specificity for chemical composition. In FIG. 1D, a model is depicted for the discrimination of phage for semiconductor heterostructures, as seen in the fluorescence and SEM images (FIGS. 1A-C).

The present invention demonstrates the powerful use of phage-display libraries to identify, develop and amplify binding between organic peptide sequences and inorganic semiconductor substrates. This peptide recognition and specificity of inorganic crystals has been extended to other substrates, including GaN, ZnS, CdS, $Fe_3O_4$, $Fe_2O_3$, CdSe, ZnSe and $CaCO_3$ using peptide libraries.

Figure 1F:
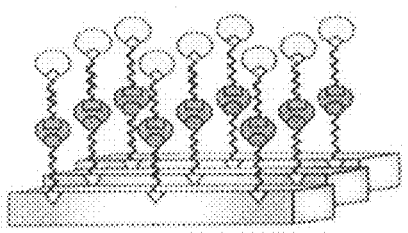

Bivalent synthetic peptides with two-component recognition (FIGS. 1E-F) are currently being designed; such peptides have the potential to direct nanoparticles to specific locations on a semiconductor structure. These organic and inorganic pairs should provide powerful building blocks for the fabrication of a new generation of complex, sophisticated electronic structures.

Metallic and Magnetic Materials

In the present invention, specific binding and recognition of binding molecules is extended in unexpected ways to metal materials including but not limited to magnetic and ferromagnetic materials, including particles and nanoparticles. A combinatorial peptide phage display library expressing a large collection of bacteriophage that expresses millions of different peptide sequences on their surfaces was combined with biopanning techniques to select specific peptide sequences that tightly and directly bind to and recognize metal materials, including magnetic materials, (e.g., Co, SmCo5, CoPt and FePt). The present inventors have found that these magnetic material binding peptides can be used to control the nucleation of inorganic materials, as has been demonstrated in nature and in the III-V and II-VI semiconductors. If proteins can be used to control the nucleation of magnetic materials, then magnetic nanoparticles could be prepared much cheaper and easier than using traditional methods. The nanomolecular magnets and magnetic material may be used, e.g., for micro or nanomachines, dynamos, generators, magnetic storage or any other applications for material that are magnetic or may be magnetized. Another use for these materials is to modify the surface of magnetic materials. The peptides can act as linkers for attaching other materials to the surface of the magnetic material, allowing the self-assembly of complex nanostructures, which could form the basis of novel electronic devices.

The present inventors have recognized that this approach of selecting binding peptides (using combinatorial peptide libraries and panning techniques) has not been used with magnetic materials, and peptides have never been used to control the nucleation of magnetic materials. There are currently many other techniques being researched to synthesize magnetic nanoparticles. All of these efforts are based on a high temperature synthesis that must be performed in an inert atmosphere using expensive reagents and often require further processing and purification after synthesis to fabricate nanoparticles with the desired shape and crystallinity. The result is that preparing magnetic nanoparticles in the traditional fashion is very expensive and not conducive to scale up. The approach presented herein can be performed at room temperatures using inexpensive reagents yielding nanoparticles with controlled crystallinity, making it a much cheaper approach to the synthesis of magnetic nanoparticles. This approach may also be used to control crystal structure and crystal orientation.

Peptide-mediated synthesis of magnetic materials provides a much cheaper and environmentally friendly approach to the synthesis of magnetic nanoparticles. The current protocol for preparing magnetic nanoparticles is both time-consuming and expensive. In addition, the current protocol yields nanoparticles that are coated with organic surfactants. These surfactants are not amicable to further modification of the nanoparticle. Advances in the field of molecular biology have enabled the functionalization of peptides, suggesting that nanoparticles grown from peptides will also be easily functionalized, which facilitates their incorporation into electronic devices and integration into magnetic memory devices.

Current techniques for preparing magnetic nanoparticles are expensive and time consuming requiring high temperatures, inert atmospheres, expensive reagents, cumbersome purifications, and post synthetic modifications. This new technique for preparing magnetic nanoparticles using peptides to mediate particle formation alleviates all of these concerns allowing much more rapid and inexpensive particle synthesis. In addition, better control of crystal structure and orientation is achievable.

Known techniques may be used to produce enough peptide to prepare large quantities of nanoparticles. Genetically designed organisms may be used to produce the peptide or peptides of interest. The peptide(s) may be manufactured in one of the coat proteins of, e.g., M13 bacteriophage. The bacteriophage may be further designed or engineered to express the protein in additional coat proteins. Furthermore, bacteria, such as *E. coli*, may be engineered to express the peptides of interest in one or more designs or at locations of interest. One distinct advantage of using peptides for localizing or positioning the magnetic materials made herein is that they do not have the limitations inherent in semiconductor processing, which is generally limited to two dimensions, e.g., using photolithography. The peptide(s) of the present invention may be used in or about a matrix that permits the three-dimensional positioning or synthesis of the peptides. These peptides may then be formed as a film, in lines or striations, layers, dots, in grooves, on the surface, sides or bottom of an opening and the like.

Magnetic nanostructures have a variety of applications, including memory devices, sensors, ferrofluids, etc. The materials, particles, and nanoparticles described herein are applicable to all of these fields.

Still further, the metallic and magnetic materials of the invention can be used in methods of use in applications which include the following. Additional applications include therapeutics, diagnostics, engineering, chemical engineering processing of reactions, cellular, and environmental applications. For example, magnetic separations can be carried out (including bulk separations in large scale processing of reaction processes). Other applications include purifications, therapeutics, biocompatibility, drug delivery, imaging contrast agents, localization (in vivo) of magnetics which are externally addressable. Drugs delivery can include the coupling of particles to drugs or chemotherapeutics followed by localization in the body by magnetic fields. Proper particle design can yield cellular penetration. Another application is blood-urine detection. In engineering applications, display devices can be made with controlled aspect ratio magnetic particles coupled to optoactive materials including fluorescent and birefringent materials. Sensor devises can be made wherein binding events change the moment of inertia for magnetic particles coupled to binding elements. The moment of inertia change can be detected through polarization decay, including use of a coupled optically active agent. Another application is in storage. For example, memory can be made wherein the readout involves response to time varying magnetic field. The writing step may involve binding of a specific moiety to a specific address. Cellular applications include cell modifications and cell triggering. In cellular modification, the size of the magnetic particle can be adjusted to allow penetration into the cell, wherein the particle is coupled with a reagent. Magnetic fields can be used as a motive force for penetration. This can be useful for transfection procedures. In cellular triggering, the reagent coupled with the magnetic particle can enter the cell and then time varying magnetic fields can be used to trigger a reponse in the cell.

Examples of magnetic separation include classical affinity based separations in-vitro and localization of reagents in-vivo. In affinity based separation, the magnetic nanoparticles can have an advantage because of the smaller size and large aspect ratio, and good control over size and shape distribution. Another advantage is if the particles have high magnetic permitivity. The particle can be long and can rotate in the magnetic field, thus generating additional forces from the shape effect. More powerful separation forces can be achieved per mg of reagent. In localization of reagents in vivo, magnetic particles can be injected or ingested coupled with reagents. External, spatially varying field can be applied to a subject causing particles to collect in the region of highest gradient B. Small size of particle plus reagent can allow for reagent to access tissues or even penetrate cells.

More particularly, the present inventors have used combinatorial peptide phage display libraries (i.e., large collections of bacterial phage that express millions of different peptide sequences on their surfaces) and biopanning techniques to select specific peptide sequences that tightly bind directly to magnetic materials ($\epsilon$-Co, CoPt, FePt). By selecting and identifying specific peptide sequences that interact with high affinity to magnetic materials, one can quickly and easily identify peptides that can potentially be used to control the nucleation of magnetic nanostructures. Using peptides to control the nucleation of magnetic nanoparticles enables the synthesis of magnetic nanostructures under ambient conditions. The traditional protocols for preparing magnetic nanoparticles often require elaborate synthetic schemes and extensive purification, implying that peptide-mediated nucleation would provide a much cheaper alternative to nanoparticle synthesis.

One of the special advantages of the present invention is that the peptides selected by this approach permit peptides to be selected to bind specifically and directly to magnetic materials. These peptides have demonstrated an ability to nucleate selectively magnetic nanostructures with controlled crystallinity. To date, Co nanoparticles have been prepared of hexagonally close packed Co, and CoPt and FePt nanoparticles have been prepared with the layered crystallinity traditionally associated with the Invar alloys. These crystal structures exhibit the largest magnetic susceptibility of their respective materials, and that these materials retain their desirable magnetic properties at the nanometer length scale. These properties make these materials excellent candidates for the fabrication of next generation magnetic memory devices.

Currently memory devices are prepared using a CoCr alloy with a density of 16.3 Gb/in2. The smaller size of these nanoparticles conceivably allows the construction of memory devices with a density in the terabit/in2 range. With the present invention, $SmCo_5$ nanoparticles are prepared that possess HCP P6/mm crystallinity.

Using peptides to control the nucleation of the nanoparticles also facilitates further functionalization of the nanoparticles. Nanoparticles prepared in the traditional fashion are often coated with hydrophobic surfactants making further functionalization (activity or active group attachments) a laborious process. Nanoparticles prepared as disclosed herein may be coated with peptides, which are relatively easy to functionalize using a variety of chemical and biological techniques, as known to those of skill in the art. Further functionalization of these nanoparticles allows their self-assembly into complex architectures and memory devices.

The particles and nanoparticles prepared using peptides to control their crystallinity possess the ability to revolutionize the magnetic recording industry due to their small size, high magnetic susceptibility and ease of preparation.

EXAMPLE I

Peptide Preparation, Isolation, Selection and Characterization

Peptide selection. The phage display or peptide library was contacted with the semiconductor, or other, crystals in Tris-buffered saline (TBS) containing 0.1% TWEEN-20, to reduce phage-phage interactions on the surface. After rocking for 1 hour at room temperature, the surfaces were washed with 10 exposures to Tris-buffered saline, pH 7.5, and increasing TWEEN-20 concentrations from 0.1% to 0.5% (v/v). The phage were eluted from the surface by the addition of glycine-HCl (pH 2.2) 10 minute, transferred to a fresh tube and then neutralized with Tris-HCl (pH 9.1). The eluted phage were titered and binding efficiency was compared.

The phage eluted after third-round substrate exposure were mixed with their *Escherichia coli* (*E. coli*) ER2537 host and plated on LB XGal/IPTG plates. Since the library phage were derived from the vector M13 mp19, which carries the lacZα gene, phage plaques were blue in color when plated on media containing Xgal (5-bromo-4-chloro-3-indoyl-β-D-galactoside) and IPTG (isopropyl-β-D-thiogalactoside). Blue/white screening was used to select phage plaques with the random peptide insert. Plaques were picked and DNA sequenced from these plates.

Substrate preparation. Substrate orientations were confirmed by X-ray diffraction, and native oxides were removed by appropriate chemical specific etching. The following etches were tested on GaAs and InP surfaces: $NH_4OH:H_2O$ (1:10), $HCl:H_2O$ (1:10), $H_3PO_4:H_2O_2:H_2O$ (3:1:50) at 1 minute and 10 minute etch times. The best element ratio and least oxide formation (using XPS) for GaAs and InP etched surfaces was achieved using $HCl:H_2O$ for 1 minute followed by a deionized water rinse for 1 minute. However, since an ammonium hydroxide etch was used for GaAs in the initial screening of the library, this etch was used for all other GaAs substrate examples. Si(100) wafers were etched in a solution of $HF:H_2O$ 1:40 for one minute, followed by a deionized water rinse. All surfaces were taken directly from the rinse solution and immediately introduced to the phage library. Surfaces of control substrates, not exposed to phage, were characterized and mapped for effectiveness of the etching process and morphology of surfaces by AFM and XPS.

Multilayer substrates of GaAs and of $Al_{0.98}Ga_{0.02}As$ were grown by molecular beam epitaxy onto GaAs(100). The epitaxially grown layers were Si-doped (n-type) at a level of $5 \times 10^{17}$ $cm^{-3}$.

Antibody and Gold Labeling. For the XPS, SEM and AFM examples, substrates were exposed to phage for 1 hour in Tris-buffered saline then introduced to an anti-fd bacteriophage-biotin conjugate, an antibody to the pIII protein of fd phage, (1:500 in phosphate buffer, Sigma) for 30 minutes and then rinsed in phosphate buffer. A streptavidin-20-nm colloidal gold label (1:200) in phosphate-buffered saline (PBS, Sigma) was attached to the biotin-conjugated phage through a biotin-streptavidin interaction; the surfaces were exposed to the label for 30 minutes and then rinsed several times with PBS.

X-ray Photoelectron Spectroscopy (XPS). The following controls were done for the XPS examples to ensure that the gold signal seen in XPS was from gold bound to the phage and not non-specific antibody interaction with the GaAs surface. The prepared GaAs(100) surface was exposed to three conditions: (1) antibody and the streptavidin-gold label, but without phage; (2) G1-3 phage and streptavidin-gold label, but without the antibody; and (3) streptavidin-gold label, without either G1-3 phage or antibody.

The XPS instrument used was a Physical Electronics Phi ESCA 5700 with an aluminum anode producing monochromatic 1,487-eV X-rays. All samples were introduced to the chamber immediately after gold-tagging the phage (as described above) to limit oxidation of the GaAs surfaces, and then pumped overnight at high vacuum to reduce sample outgassing in the XPS chamber.

Atomic Force Microscopy (AFM). The AFM used was a Digital Instruments Bioscope mounted on a Zeiss Axiovert 100s-2tv, operating in tip scanning mode with a G scanner. The images were taken in air using tapping mode. The AFM probes were etched silicon with 125-mm cantilevers and spring constants of $20\pm100$ $Nm^{-1}$ driven near their resonant frequency of $200\pm400$ kHz. Scan rates were of the order of $1\pm5$ $mms^{-1}$. Images were leveled using a first-order plane to remove sample tilt.

Transmission Electron Microscopy (TEM). TEM images were taken using a Philips EM208 at 60 kV. The G1-3 phage (diluted 1:100 in TBS) were incubated with GaAs pieces (500 mm) for 30 minutes, centrifuged to separate particles from unbound phage, rinsed with TBS, and resuspended in TBS. Samples were stained with 2% uranyl acetate.

Scanning Electron Microscopy (SEM). The G12-3 phage (diluted 1:100 in TBS) were incubated with a freshly cleaved hetero-structure surface for 30 minutes and rinsed with TBS. The G12-3 phage were tagged with 20 nm colloidal gold. SEM and elemental mapping images were collected using the Norian detection system mounted on a Hitachi 4700 field emission scanning electron microscope at 5 kV.

EXAMPLE II

Biofilms

The present inventors have recognized that organic-inorganic hybrid materials offer new routes for novel materials and devices. Size controlled nanostructures give optically and electrically tunable properties of semiconductor materials and organic additives modify the inorganic morphology, phase, and nucleation direction. The monodispersed nature of biological materials makes the system compatible for highly ordered smectic-ordering structure. Using the methods of the present invention, highly ordered nanometer scale as well as multi-length scale alignment of II-VI semiconductor material using genetically engineered, self-assembling, biological molecules, e.g., M13 bacteriophage that have a recognition moiety of specific semiconductor surfaces were created.

Using the compositions and methods of the present invention nano- and multi-length scale alignment of semiconductor materials was achieved using the recognition and self-ordering system described herein. The recognition and self-ordering of semiconductors may be used to enhance micro fabrication of electronic devices that surpass current photolithographic capabilities. Application of these materials include: optoelectronic devices such as light emitting displays, optical detectors and lasers; fast interconnects; and nano-meter scale computer components and biological sensors. Other uses of the biofilms created using the present invention include well-ordered liquid crystal displays and organic-inorganic display technology.

The films, fibers and other structures may even include high-density sensors for detection of small molecules including biological toxins. Other uses include optical coatings and optical switches. Optionally, scaffoldings for medical implants or even bone implants; may be constructed using one or more of the materials disclosed herein, in single or multiple layers or even in striations or combinations of any of these, as will be apparent to those of skill in the art.

Other uses for the present invention include electrical and magnetic interfaces, or even the organization of 3D electronic nanostructures for high-density storage, e.g., for use in quantum computing. Alternatively, high density and stable storage of viruses for medical application that can be reconstituted, e.g., biologically compatible vaccines, adjuvants and vaccine containers may be created with the films and or matrices created with the present invention. Information storage based on quantum dot patterns for identification, e.g., department of defense friend or foe identification in fabric of armor or coding. The present nanofibers may even be used to code and identify money.

Building well-ordered, well-controlled, two and three dimensional structure at the nanolength scale is the major goal of building next generation optical, electronic and magnetic materials and devices. Current methods of making specific nanoparticles are limited in terms of both length scale and the types of materials. The present invention exploits the properties of self-assembling organic or biological molecules or particles, e.g., M13 bacteriophage to expand the alignment, size, and scale of the nanoparticles as well as the range of semiconductor materials that can be used.

The present inventors have recognized that monodisperse biomaterials having anisotropic shapes are an alternative way to build well-ordered structures. Nano- and multi-length scale alignment of II-VI semiconductor material were accomplished using genetically engineered M13 bacteriophage that possess a recognition moiety (a peptide or amino acid oligomer) for specific semiconductor surfaces.

Seth and coworkers have characterized Fd virus smectic ordering structures that have both a positional and directional order. The smectic structure of Fd virus has potential application in both multi-scale and nanoscale ordering of structures to build 2-dimensional and 3-dimensional alignment of nanoparticles. Bacteriophage M13 was used because it can be genetically modified, has been successfully selected to have a shape identical to the Fd virus, and has specific binding affinities for II-VI semiconductor surfaces. Therefore, M13 is an ideal source for smectic structure that can serve in multi-scale and nanoscale ordering of nanoparticles.

The present inventors have used combinatorial screening methods to find M13 bacteriophage containing peptide inserts that are capable of binding to semiconductor surfaces. These semiconductor surfaces included materials such as zinc sulfide, cadmium sulfide and iron sulfide. Using the techniques of molecular biology, bacteriophage combinatorial library clones that bind specific semi-conductor materials and material surfaces were cloned and amplified up to concentrations high enough for liquid crystal formation.

The filamentous bacteriophage, Fd, has a long rod shape (length: 880 nm; diameter: 6.6 nm) and monodisperse molecular weight (molecular weight: $1.64 \times 10^7$). These properties result in the bacteriophage's lyotropic liquid crystalline behavior in highly concentrated solutions. The anisotrophic shape of bacteriophage was exploited as a method to build well-ordered nanoparticle layers by use of biological selectivity and self-assembly. Monodisperse bacteriophage were prepared through standard amplification methods. In the present invention, M13, a similar filamentous bacteriophage, was genetically modified to bind nanoparticles such as zinc sulfide, cadmium sulfide and iron sulfide.

Mesoscale ordering of bacteriophage has been demonstrated to form nanoscale arrays of nanoparticles. These nanoparticles are further organized into micron domains and into centimeter length scales. The semiconductor nanoparticles show quantum confinement effects, and can be synthesized and ordered within the liquid crystal.

Bacteriophage M13 suspension containing specific peptide inserts were made and characterized using AFM, TEM, and SEM. Uniform 2D and 3D ordering of nanoparticles was observed throughout the samples.

Figure 2:
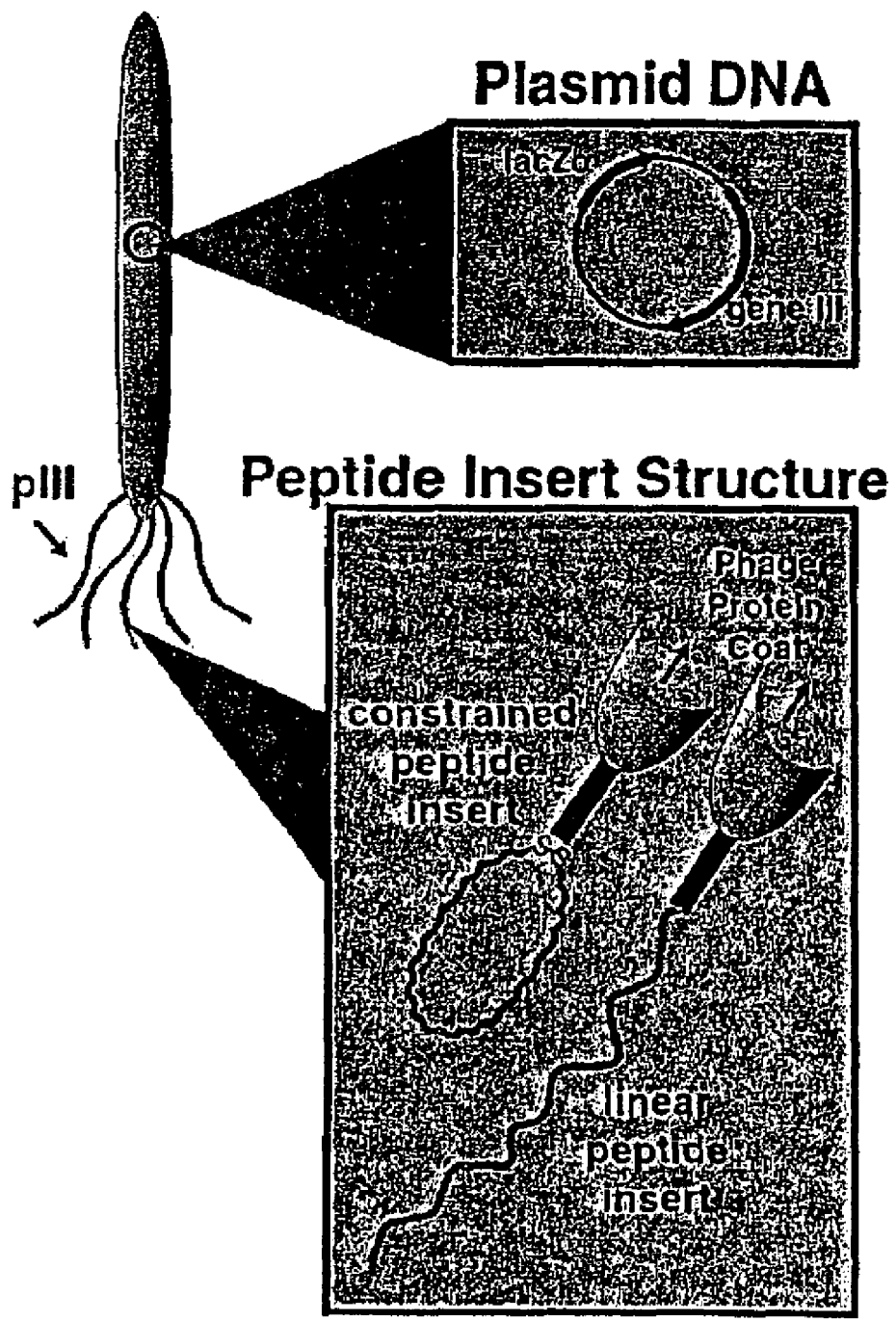
FIG. 2 depicts schematic diagrams of the smectic alignment of M13 phages in accordance with the present invention.

AFM. Includes Digital Instruments Bioscope mounted on a Zeiss Axiovert 100s-2tv, operating in tip scanning mode with a G scanner. The images were taken in air using tapping mode. The AFM probes were etched silicon with 125 mm cantilevers and spring constants of $20 \pm 100$ $Nm^{-1}$ driven near their resonant frequency of $200 \pm 400$ kHz. Scan rates were of the order of $1 \pm 5$ $mms^{-1}$. Images were leveled using a first-order plane to remove sample tilt. FIGS. 2A and 2B are schematic diagrams of the smectic alignment of M13 phages observed using AFM.

TEM. TEM images were taken using a Philips EM208 at 60 kV. The G1-3 phage (diluted 1:100 in TBS) were incubated with semiconductor material for 30 minutes, centrifuged to separate particles from unbound phage, rinsed with TBS, and resuspended in TBS. Samples were stained with 2% uranyl acetate.

SEM. The phage (diluted 1:100 in TBS) were incubated with a freshly cleaved hetero-structure surface for 30 minutes and rinsed with TBS. The G12-3 phage were tagged with 20 nm colloidal gold. SEM and elemental mapping images were collected using the Norian detection system mounted on a Hitachi 4700 field emission scanning electron microscope at 5 kV.

Genetically engineered M13 bacteriophage that had specific binding properties to semiconductor surfaces was amplified and purified using standard molecular biological techniques. 3.2 mL of bacteriophage suspension (concentration: ~$10^7$ phages/μL) and 4 mL of overnight culture were added to 400 mL LB medium for mass amplification. After amplification, ~30 mg of pellet was precipitated. The suspensions were prepared by adding $Na_2S$ solutions to $ZnCl_2$ doped A7 phage suspensions at room temperature. The highest concentration of A7-phage suspension was prepared by adding 20 μL of 1 mM $ZnCl_2$ and $Na_2S$ solutions, respectively into the ~30 mg of phage pellet. The concentration was measured using extinction coefficient of 3.84 mg/mL at 269 nm.

As the concentration of the isotropic suspension is increased, nematic phase that has directional order, cholesteric phase that has twisted nematic structure, and smectic phase that has directional and positional orders as well, are observed. These phases had been observed in Fd viruses that did not have nanoparticles.

Polarized optical microscopy (POM). M13 phage suspensions were characterized by polarized optical microscope. Each suspension was filled to glass capillary tube of 0.7 mm diameter. The highly concentrated suspension (127 mg/mL) exhibited iridescent color [5] under the paralleled polarized light and showed smectic texture under the cross-polarized light (FIG. 3A). The cholesteric pitches in FIG. 3B can be controlled by varying the concentration of suspension as shown in TABLE 2. The pitch length was measured and the micrographs were taken after 24 hours later from the preparation of samples.

TABLE 2

Cholesteric pitch and concentration relationship.

| Concentration (mg/ml) | Pitch length (um) |
|---|---|
| 76.30 | 31.9 |
| 71.22 | 51.6 |
| 56.38 | 84.8 |
| 50.52 | 101.9 |
| 43.16 | 163.7 |
| 37.04 | 176.1 |
| 27.54 | 259.7 |

AFM. For AFM observation, 5 µL of M13 suspension (concentration: 30 mg/mL) of M13 bacteriophage suspension was dried for 24 hours on the 8 mm×8 mm mica substrate that was silated by 3-amino propyl triethyl silane for 4 hours in the dessicator. Images were taken in air using tapping mode. Self-assembled ordering structures were observed due to the anisotropic shape of M13 bacteriophage, 880 nm in length and 6.6 nm in width. In FIG. 3C, M13 phage lie in the plane of the photo and form smectic alignment.

SEM. For SEM observation, the critical point drying samples of bacteriophage and ZnS nanoparticles smectic suspension (concentration of bacteriophage suspension 127 mg/mL) were prepared. In FIG. 3D, nanoparticles rich areas and bacteriophage rich areas were observed. The length of the separation between nanoparticles and bacteriophage correspond to the length of bacteriophage. The ZnS wurzite crystal structure was confirmed by electron diffraction pattern using dilution sample of the smectic suspension with TEM (FIGS. 3E and 3F).

Figure 4A:
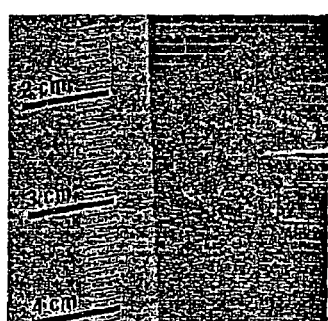
FIG. 4 include images of the M13 bacteriophage nanoparticle as (A) photograph of the film, (B) schematic diagram of the film structure, (C) AFM image, (D) SEM image, (E-F) TEM images along the x-z and z-y planes.
Figure 4B:
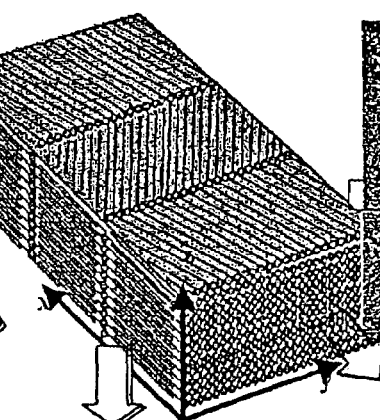

Preparation of the Biofilm. Bacteriophage Pellets were suspended with 400 µL of Tris-buffered saline (TBS, pH 7.5) and 200 µL of 1 mM $ZnCl_2$ to which 1 mM $Na_2S$ was added. After rocking for 24 hours at room temperature, the suspension (contained in a 1 mL eppindorff tube) was slowly dried in a dessicator for one week. A semi-transparent film ~15 µm thick was formed on the inside of the tube. This film, shown in FIG. 4A, was carefully taken using a tweezers. A schematic diagram of the biofilm is shown in FIG. 4B.

SEM observation of biofilm. Nanoscale bacteriophage alignment of the A7-ZnS film were observed using SEM. In order to carry out SEM analysis the film was cut then coated via vacuum deposition with 2 nm of chromium in an argon atmosphere. Highly close-packed structures, FIG. 4D were observed throughout the sample. The average length of individual phage, 895 nm is reasonable analogous to that of phage, 880 nm. The film showed the smectic like A- or C-like lamellar morphologies that exhibited periodicity between the nanoparticle and bacteriophage layers. The length of periodicity corresponded to that of the bacteriophage. The average size of nanoparticle is ~20 nm analogous to the TEM observation of individual particles.

TEM observation of biofilm. ZnS nanoparticle alignment was investigated by embedding the film in epoxy resin (LR white) for one day and polymerized by adding 10 µl of accelerator. After curing, the resin was thin sectioned using a Leica Ultramicrotome. These ~50 nm sections were floated on distilled water, and picked up on blank gold grids. Parallel-aligned nanoparticles in a low, which corresponded to x-z plane in the schematic diagram, were observed, FIG. 4 E-F. Since each bacteriophage had 5 copies of the A7 moieties, each A7 recognize one nanoparticle (2~3 nm size) and aligned approximately 20 nm in a width and extended to more than two micrometers in length. The two micrometers by 20 nm bands formed in parallel each band separated by ~700 nm. This discrepancy may come from the tilted smectic alignment of the phage layers with respect to observation in the TEM, which is reported by Marvin group. A y-z axis like nanoparticle layer plane was also observed similar to that shown in FIG. 1F. The SAED patterns of the aligned particles showed that the ZnS particles have the wurzite hexagonal structure.

Figure 4C:
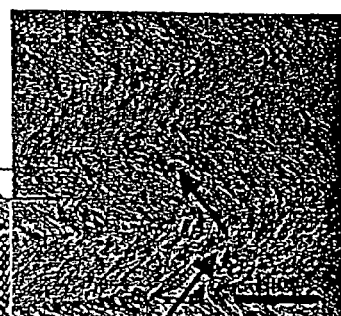
Figure 4D:
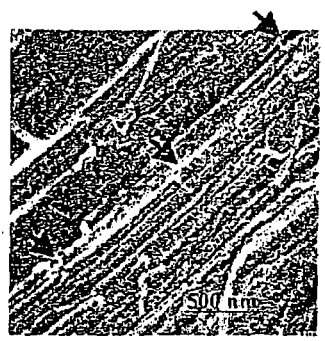
Figure 4E:
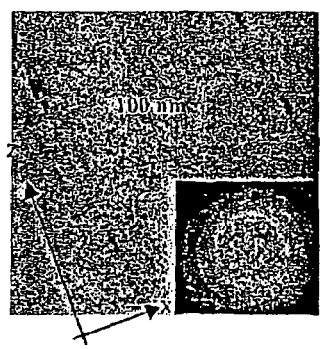
Figure 4F:
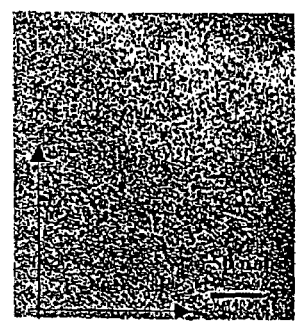

AFM observation of biofilm: The surface orientation of the viral film was investigated using AFM. In FIG. 4C, phage were shown to have formed an parallel aligned herringbone pattern that have almost right angle between the adjacent director normal (bacteriophage axis) on most of surface that is named as smectic O. The film showed long range ordering of normal director that is persistent to the tens of micrometers. In some of areas where two domain layers meet each other, two or three multi-length scale of bacteriophage aligned paralleled and persistent to the smectic C ordering structure.

Nano and multi-length scale alignment of semiconductor materials using the recognition and as well as self-ordering system enhances the future microfabrication of electronic devices. These devices have the potential to surpass current photolithographic capabilities. Other potential applications of these materials include optoelectronic devices such as light-emitting displays, optical detectors, and lasers, fast interconnects, nano-meter scale computer component and biological sensors.

EXAMPLE III

Formation of Metallic and Magnetic Materials

A phage display technique was used to discover novel peptides that bind selectively to magnetic materials. In these particular studies, films of the magnetic materials were prepared by first synthesizing colloidal dispersions of the magnetic materials. These colloidal solutions were then drop coated onto Si wafers and annealed under $N_2$ to generate the desired crystal structure. Phage display was then performed on these films (ε-Co, CoPt, and FePt), and peptides were discovered that bind selectively to each substrate. These peptides were then used to nucleate unique nanoparticles by mixing the phage expressing the peptide of interest, the metal salt, and a reducing agent.

The synthesis of nanoparticles with controlled size and composition is of fundamental and technological interest. In the last few years there has been a flurry of papers describing the synthesis of nanoparticles composed of metals and semiconductors with remarkable control over the size and shape of the resulting nanoparticles. Recently it has been shown that peptides identified via phage display can bind selectively to inorganic surfaces and can be used to control the nucleation of semiconducting nanoparticles. In this case, the peptides can control the size, shape, composition, and even the crystallinity of the resulting nanoparticles. Due to the success of peptides in controlling the synthesis of semiconducting nanoparticles, there is a great deal of interest in applying the technology to other materials of interest.

One particularly interesting and commercially useful class of materials is ferromagnets, including particles and nanoparticles. Ferromagnetic materials are the cornerstone of the billion dollar per year magnetic recording industry. Current devices use a CoCr alloy for data storage because of the high magnetic susceptibility and ease of preparation. Other materials are currently in development. One such material is metallic Co, which has a magnetic anisotropy in the range of $10^7$ ergs/cm$^3$. This high magnetic anisotropy suggests that particles as small as 10 nm in diameter, can act as single domains and function as memory elements. Current technology uses memory elements with a domain size that is in the range of hundreds of nanometers, so generating Co nanoparticles in the 10 nm size range would be a dramatic improvement that would lead to much denser memory devices. More interesting ferromagnetic materials are the magnetic alloys of Pt, specifically FePt and CoPt. These materials have very large magnetic anisotropies ($10^8$ ergs/cm$^3$), due to the Invar effect, in which perturbations in the lattice constant caused by the layering of Fe and Pt atoms causes the Pt to develop a magnetic state. The large anisotropy possessed by these systems suggests that nanoparticles as small as 2 nm can act as ferromagnets at room temperature, implying that they can be used in the development of very high-density memory devices.

Due to the large magnetic anisotropies of these systems, a great deal of effort has been invested in the synthesis of particles and nanoparticles composed of these materials. Several different synthetic protocols have been developed for ε-Co, FePt and CoPt and they all possess the same fundamental weaknesses. All of these synthetic strategies rely on the restricted precipitation of nanoparticles in the presence of surfactants at elevated temperatures. All of these nanoparticle preparations must be performed in an inert atmosphere with expensive reagents, making them very expensive and not amicable to scale up. Furthermore, these preparations often require further modifications of the particles, including high temperature annealing to attain the desired crystallinity, and size selective precipitation to acquire monodisperse populations of particles. These extra synthetic steps increase the cost of these synthetic strategies.

Since these materials are commercially important, a novel synthetic strategy was desired. Applying the principle of peptide-mediated synthesis to magnetic materials provides such an alternative. In these studies phage display selection was performed on the magnetic materials of interest (Co, CoPt, SmCo5, and FePt) to identify peptides that specifically bind to the magnetic materials with high affinity. After characterization, these peptides were then used to control the nucleation of magnetic nanoparticles. In these studies, phage expressing the peptides of interest were mixed with the metallic salts of the metals of interest. A reducing agent (NaBH4) was then added to generate the nanoparticles. The nanoparticles were formed and characterized using TEM. The synthesis of the present invention was performed under ambient conditions to provide a much cheaper alternative to existing synthetic strategies for generating magnetic nanoparticles.

X-Ray Diffraction Analysis of Magnetic Nanoparticles

Magnetic surfaces had to be generated to use as substrates in the phage display. To accomplish this, magnetic nanoparticles were prepared in the traditional fashion, and drop coated onto Si wafers. Before the phage display studies were begun, the surfaces were characterized with x-ray diffraction (XRD) to ensure the material possessed the appropriate crystallinity.

The XRD pattern obtained for ε-Co correlated well with patterns obtained from the literature, displaying a triplet of peaks between 45 degrees and 50 degrees that are particularly distinctive because they correspond to the (221), (310), and (311) crystal planes of ε-Co. The FePt and CoPt patterns also agreed with the literature spectra for FePt11 with peaks corresponding to the (001), (110), (111), (200), (002), (210), (112), and (202) planes of FePt and CoPt. The XRD on SmCo5 agreed with literature values for HCP SmCo5 with peaks representing the (101), (110), and (111) facets. This is the first reported synthesis of HCP SmCo5 nanoparticles. FIG. 5A is a high resolution TEM image of a SmCo5 nanoparticle and FIG. 5B is a selected area of the TEM image showing the electron diffraction pattern. Several spots in the diffraction pattern correlate well with the known facets of HCP SmCo5 (FIG. 5IB). FIG. 5C is a STEM image of the annealed SmCo5 nanoparticles and illustrates their size, shape, and overall morphology.

Sequence Analysis and Binding Assays of Binding Phage

TABLE 3 lists all of the peptides that were selected using phage display for their ability to bind to the magnetic materials of interest.

TABLE 3

Selected clones with magnetic binding properties.

| Material | 7-Constrained Sequence | 12 mer Sequence |
|---|---|---|
| ε-Co | * | ALSPHSAPLTLY (SEQ ID NO.:15) |
| CoPt | NAGDHAN (SEQ ID NO.:12) | SVSVGMKPSPRP (SEQ ID NO.:16) |
| FePt | SKNSNIL (SEQ ID NO.:13) | HNKHLPSTQPLA (SEQ ID NO.:17) |
| SmCo5 | TKPSVVQ (SEQ ID NO.:14) | WDPYSHLLQHPQ (SEQ ID NO.:18) |

* No consensus sequence was obtained for the 7-constrained library on ε-Co.

All of the selected sequences appear to be valid sequences that should possess high affinity for the metallic surfaces. Histidine residues appear in several of the sequences. Due to its imidazole side group, histidine is an excellent ligand for metals, so its presence in these sequences is expected. With the exception of the 7-constrained sequence on CoPt, all of the sequences isolated for the Pt alloys contain a lysine residue. Lysine-Pt interactions are believed to be important in the function of cisplatin, an important anticancer drug. The Lysine-Pt interaction suggests that these sequences bind selectively to these materials, however, the present invention is not limited to any mechanism of interaction, known or unknown.

Figure 6A:
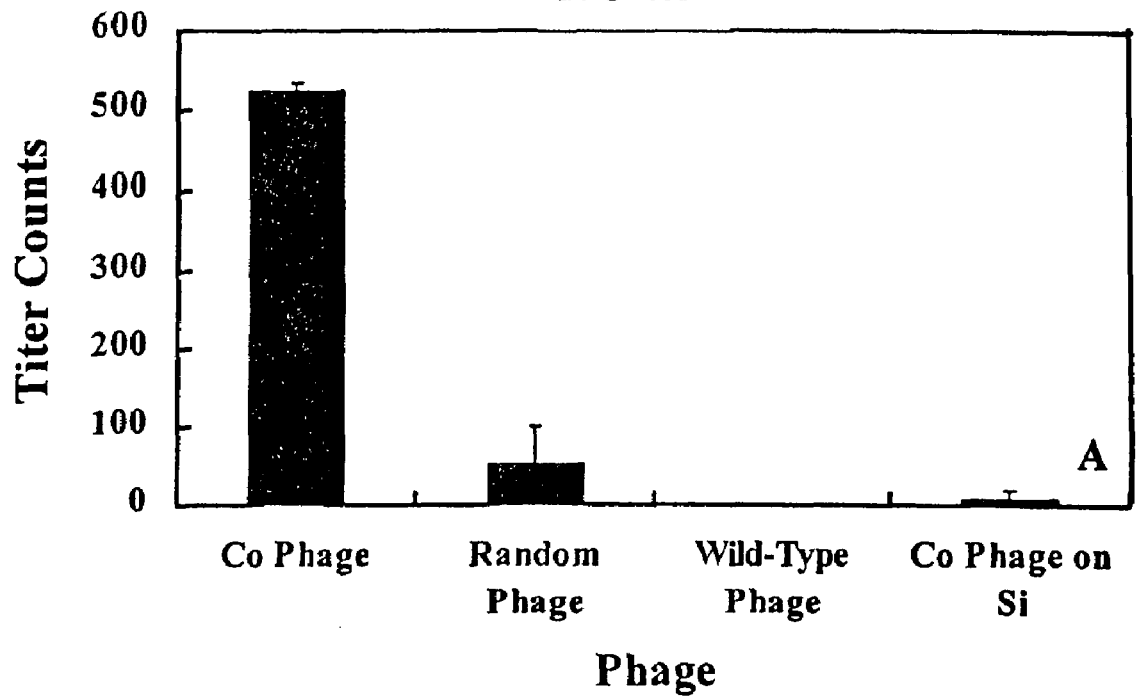
FIG. 6 are examples of binding assays illustrating (A) the specificity of the Co-specific phage for Co and (B) an isotherm of the Co-specific phage on Co in accordance with the present invention.
Figure 6B:
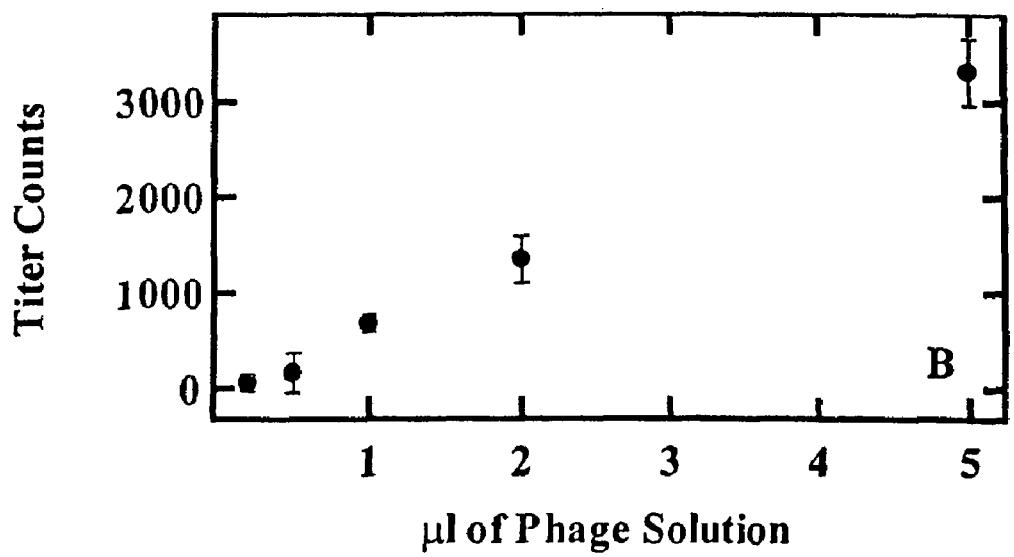

Specific Binding Assays. To determine the affinity of the isolated phage for the magnetic substrate, two studies were performed. In the first study several different peptide-containing phage were exposed to a Co surface including our Co specific phage, a random phage, and wild type phage. Additionally, the Co-specific phage was exposed to several different material surfaces. The results are depicted in FIG. 6. The Co-specific phage possessed a relative higher affinity for Co than either the wild-type phage or a random phage library sequence (FIG. 6A). Additionally, the Co-specific phage displayed a greater affinity for Co than for Si, suggesting they bound preferentially to the Co surface.

In the second study a Co surface was immersed into a solution of the Co-specific phage. This study was repeated at several different concentrations of phage. Plotting the amount of adsorbed phage vs. the concentration of phage (FIG. 6B) indicated that the adsorption of phage onto the Co surface followed the Langmuir model for adsorption of analytes on a surface. Since the adsorption is Langmuirian, generating a reciprocal plot revealed a linear correlation between the adsorbed phage and the concentration (not shown). The slope of this line is equal to the binding constant, and in the case of Co, the phage possessed a $k_{ads}$ of $2\times10^{-12}$ M. This is the first measurement of the thermodynamic properties associated with the binding between a phage and an inorganic surface, making it difficult to interpret, but the magnitude of this binding constant is comparable to several other biological interactions. This approach may be used for the CoPt and FePt systems.

Both studies showed that the peptides selected using phage display screening possessed specific binding towards Co and not towards other materials. It is this specificity that can be used to direct metal materials formation, including magnetic materials.

TEM Analysis of Nanoparticles Prepared Through Peptide-Mediated Nucleation

In one embodiment of the present invention, nanoparticles were prepared using peptides to modify and/or control crystallinity. High resolution TEM images of CoPt nanoparticles grown using the 7-constrained sequence are shown in TABLE 3 were also taken (not shown). These nanoparticles had lattice spacings of 0.19 and 0.22 nm, which correlates with the lattice spacing of L10 CoPt.

High resolution TEM images of nanoparticles grown using wild type phage were also taken as were images of CoPt nanoparticle grown using phage with a random peptide insert (not depicted). In both control studies, nanoparticles still form, but they lacked the crystallinity that the particles grown with the CoPt selective peptide possess. Nanoparticles grown in the absence of phage aggregate and precipitate out of solution, making TEM imaging nearly impossible.

High-resolution TEM images were also taken of FePt nanoparticles grown using the phage that expresses the 12mer peptide, which is selective for FePt (not depicted). These nanoparticles exhibited similar lattice spacing to the CoPt nanoparticles suggesting they are composed of L10 FePt. Electron diffraction patterns were taken of these same particles, e.g., FePt nanoparticles grown in the presence of wild type phage (not depicted). Again, these nanoparticles lack the crystallinity of the nanoparticles grown with the FePt selective phage. Also, nanoparticles grown in the absence of phage aggregate and precipitate out of solution before they could be imaged.

Figure 7A:
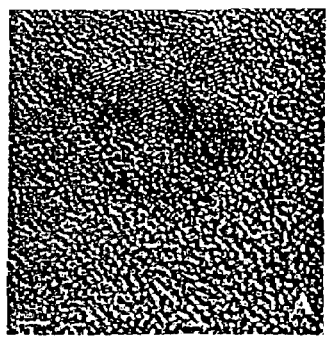
FIG. 7 includes a series of high resolution TEM images of CoPt nanoparticles prepared using (A) phage that express the 7-constrained peptide that selectively binds to CoPt, (B) phage that express a random peptide, and (C) wild-type phage.
Figure 7B:
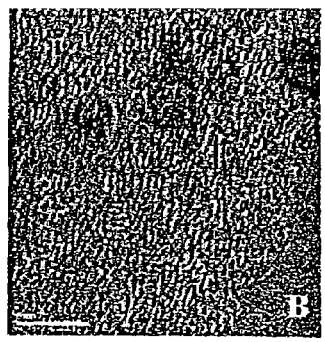
Figure 7C:
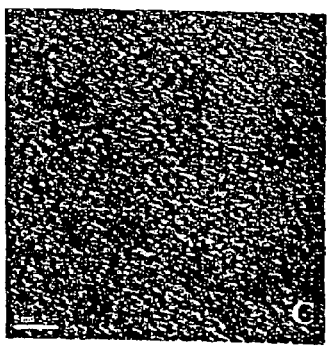

High resolution TEM images of CoPt nanoparticles grown using the 7-constrained sequence from Table 1 are shown in FIG. 7. The lattice spacing in these nanoparticles is at or about 0.22 nm and correlating well with literature values for HCP Co of approximately 0.19 nm (FIG. 7A) and with the lattice spacing of $L1_0$ CoPt. A selected area was also used to observe the electron diffraction pattern of the nanoparticles (not shown). Several bands were present in the diffraction pattern that correlate with the facets of HCP Co and indicate that the nanoparticles were, in fact, composed of HCP Co. In control experiments with either wild-type phage (FIG. 7C), nonspecific phage (FIG. 7B), nanoparticles still form, but lack the crystallinity that the particles grown with the CoPt selective peptide possess. Nanoparticles grown in the absence of phage aggregate and precipitate out of solution, making TEM imaging nearly impossible.

FIG. 8 shows high resolution TEM images of Co nanoparticles grown using the phage that expressed the 12mer peptide that binds specifically to Co (FIG. 8A). The lattice spacing in these particles is 0.2 nm, which correlates well with the literature values for HCP Co (0.19 nm). A selected area is chosen for electron diffraction pattern for these nanoparticles (FIG. 8B). Several bands are present in the diffraction pattern that correlate with the facets of HCP Co, indicating that the nanoparticles are composed of HCP Co. In control experiments involving either wild-type phage, nonspecific phage, or no phage, Co particles aggregate and sediment out of solution (not shown).

Figure 9A:
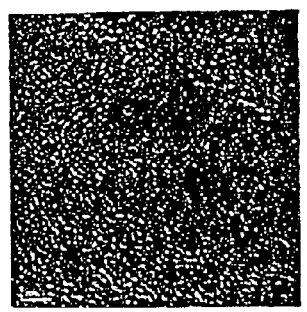
FIG. 9 are (A) high resolution TEM image of FePt nanoparticles that have been grown using phage that express a 12mer peptide and are selective for FePt, wherein (B) shows the electron diffraction pattern both of which are compared to (C) FePt nanoparticles grown using wild-type phage.
Figure 9B:
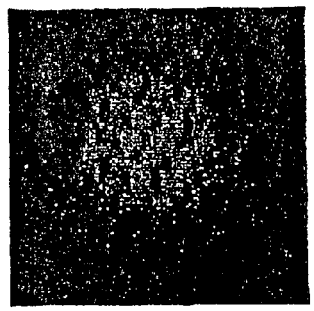
Figure 9C:
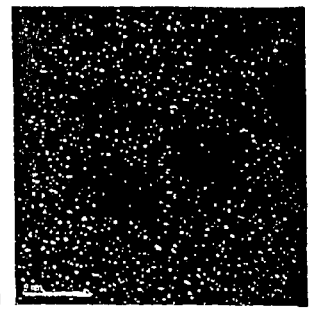

FIG. 9A shows a high resolution TEM image of FePt nanoparticles grown using phage that expressed a 12mer peptide selective for FePt. These nanoparticles exhibit similar lattice spacing to the CoPt nanoparticles and were likely composed of $L1_0$ FePt. FIG. 9B is the corresponding electron diffraction pattern, and FIG. 9C an image of FePt nanoparticles grown in the presence of wild type phage. In the absence of wild-type phage, nanoparticles lacked the crystallinity of the nanopaticles grown with the FePt-selective phage. In addition, nanoparticles grown in the absence of phage aggregated and precipitated out of solution before they can be imaged.

Figure 10A:
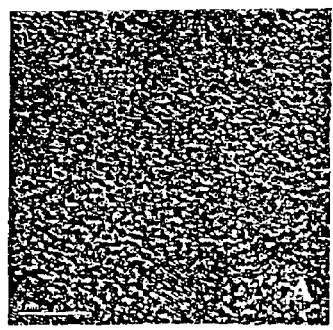
FIG. 10 is (A) high resolution TEM image of SmCo5 nanoparticles grown using a 12mer that selectively binds SmCo5 as a template, (B) an electron diffraction pattern of a selected area of (A) and (C) SmCo5 nanoparticles grown using wild-type phage as a control.
Figure 10B:
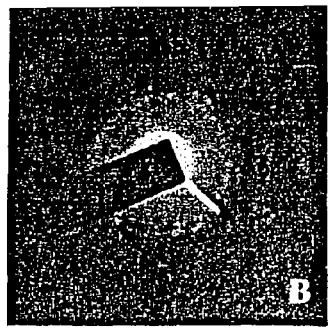
Figure 10C:
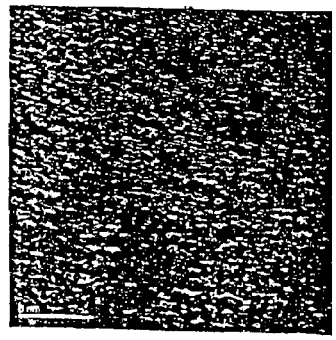

High resolution TEM images were also taken of SmCo5 nanoparticles grown using phage that expresses the 12mer peptide that is specific to SmCo5 (FIG. 10A). A selected area was used to observe the electron diffraction pattern (FIG. 10B). Again, the diffraction pattern showed several bands that correlated with the facets of HCP SmCo5. Control experiments performed with the SmCo5 system yielded results similar to that observed for the Co system, such that nanoparticles aggregated and/or precipitated out of solution when nonspecific phage were used. TEM images of such particles showed some crystalline domains, but the majority of the material was amorphous.

MFM Characterization of Nanoparticles

Figure 11A:
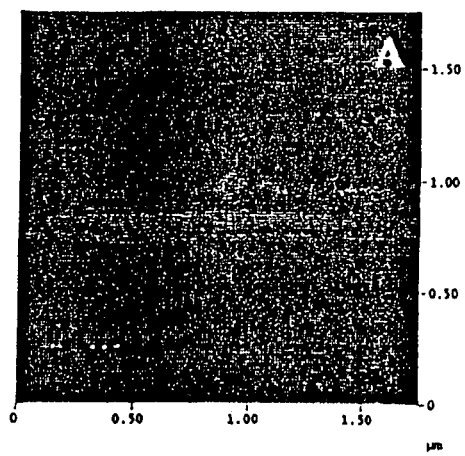
FIG. 11 is (A) an AFM image of Co-specific phage with Co nanoparticles bound to its P3 protein and (B) the corresponding MFM image.
Figure 11B:
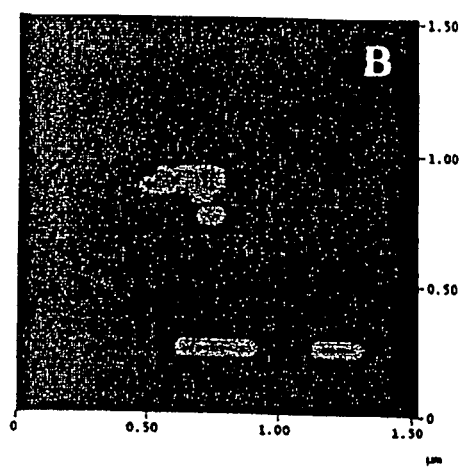

Magnetic Force Microscopy (MFM) was used to characterize the magnetic properties of the nanoparticles. Atomic force images of phage that were used to nucleate Co nanoparticles were first taken (FIG. 11A). A large aggregate of nanoparticles was evident at the end of the phage, indicating that the P3 proteins were controlling the nucleation of the nanoparticles as expected. Corresponding MFM image was taken to confirm these results (FIG. 11B)). Here, the phage could not be seen because they were non-magnetic, but the aggregate of nanoparticles was still clearly visible, indicating the nanoparticles possess a high degree of magnetic anisotropy.

Figure 12A:
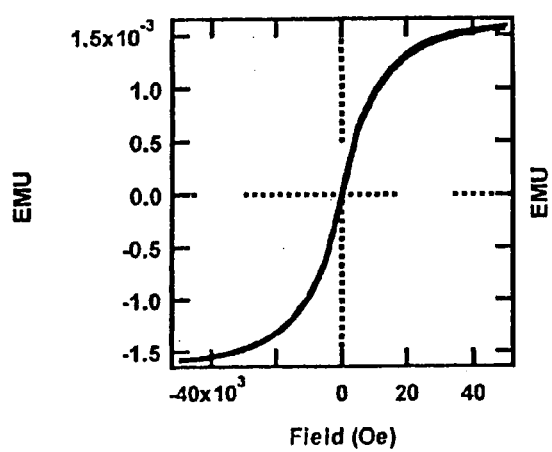
FIG. 12 is (A) a hysteresis loop of biologically prepared FePt nanoparticles and (B) a higher resolution scan of the central portion of the loop to clarify the coercivity.
Figure 12B:
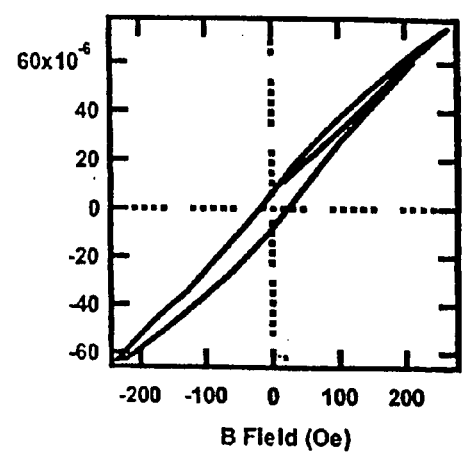
Figure 13A:
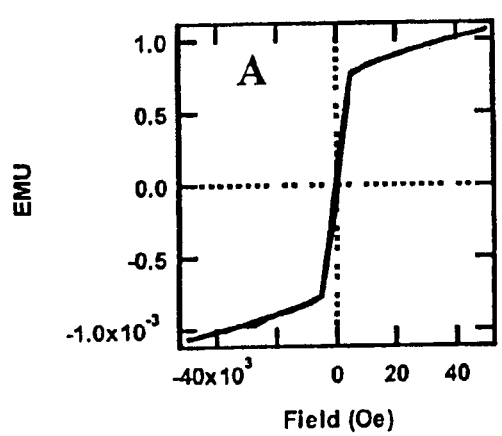
FIG. 13 is (A) a hysteresis loop of biologically prepared SmCo5 nanoparticles and (B) the central portion of the loop plotted on a smaller axis to clarify the coercivity.
Figure 13B:
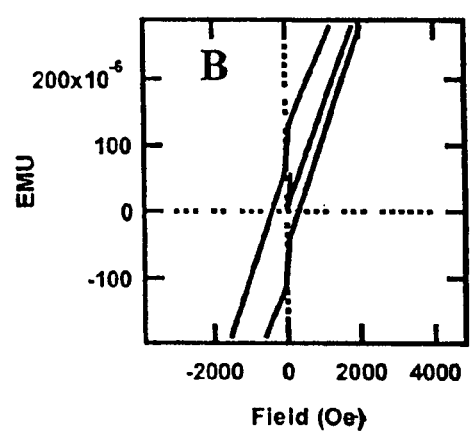

SQUID. In one embodiment of the present invention, the magnetic properties of the nanoparticles may be quantified using a Superconducting Quantum Interference Device (SQUID) magnetometer. SQUID magnetometry was used to further characterize the particles. With SQUID, a room temperature hysteresis loop for FePt nanoparticles grown using the 12mer peptide expressed on phage was taken (FIG. 12A). A high-resolution hysteresis loop of the central portion of the scan was also taken to clarify the presence of the coercivity (FIG. 12B). These samples possessed relatively low coercivity (approximately 50 Oe). The data represents the first example of ferromagnetic nanoparticles grown under ambient conditions. Hysteresis loops were also measured on biologically prepared $SmCo_5$ nanoparticles (FIG. 13). The hystersis was much larger for these nanoparticles (400 Oe). This result was expected since macroscopic samples of $SmCO_5$ typically display higher coercivity values than FePt.

Magnetic-Specific Peptides on P8 Coat Proteins

In one embodiment of the present invention, nanoparticles with magnetic behaviors are prepared using the material-specific phage that were expressed on the p3 protein of M13 bacteriophage. The p3 protein is only present on one end of the rod-shaped phage and is present in limited numbers (3-5 copies per phage). Alternatively, the p8 coat protein is expressed along the length of the phage, and there are hundreds of copies per phage. For this reason, the p8 protein was engineered to express a CoPt-specific peptides, and CoPt nanoparticles were nucleated along the length of the phage. One example of the material preparation is presented below. Other methodologies apparent to those of ordinary skill in the art of material and biologic sciences may be used without undue experimentation.

Upon nucleation of magnetic materials, including magnetic particles and nanoparticles, the peptides, with or without phage, can be heated to sufficiently high temperatures to burn off and eliminate the binding molecules associated with the scaffold in a high temperature annealing process. For example, heating to 500° C. or 1,000° C. can be carried out for times which provide optimum burn off and elimination. The temperatures can be also in the range for metal annealing, whereby polycrystalline domains can fuse into single crystalline domains.

Methodology.

Materials. Samarium (III) Chloride, Platinum (II) Acetylacetonate (Pt (Acac)$_2$, Dihydrogen Hexachloroplatinate ($H_2PtCl_6$), and Cobalt Octacarbonyl ($CO_2(CO)_8$) were purchased from Alfa Aesar. Iron Pentacarbonyl ($Fe(CO)_5$), Cobalt (II) Chloride ($CoCl_2$), Iron (II) Chloride ($FeCl_2$), Trioctylphosphine oxide (TOPO), Sodium Borohydride ($NaBH_4$), oleyl amine, and oleic acid were purchased from Aldrich.

Nanoparticle Synthesis of ε-Co. Co nanoparticles were prepared by first dissolving 0.6 g of $CO_2$ $(CO)_8$ in 5 mL of o-dichlorobenzene. This mixture was stirred for one hour to dissolve the Co and 20 mL of o-dichlorobenzene, 0.416 g of TOPO, and 0.2 mL of oleic acid were mixed in a 500 mL three-necked reaction vessel under Ar. This mixture was then heated to 100 degrees Centigrade. The mixture was then exposed to vacuum for 5 minutes to remove any dissolved $O_2$ and $H_2O$. The mixture was then heated to boiling (180 degrees Centigrade), and Co solution was added. The mixture turned black and generated a cloud of CO gas. After 20 minutes of refluxing, the reaction was cooled to room temperature. To purify the particles, 3 mL of Co nanoparticle solution was mixed with 3 mL of ethanol. After 1 hour, the mixture was centrifuged at 10,000 rpm for 5 minutes. The precipitant was resuspended in 3 mL of $CH_2Cl_2$ followed by 3 ml of ethanol and the centrifugation step was repeated. The precipitant was then resuspended in 3 mL of $CH_2Cl_2$.

Nanoparticle Synthesis of FePt. 20 mL of phenyl ether, 0.205 g of Pt(Acac)$_2$, and 0.358 g of 1,2-tetradecanediol were mixed and heated to 100 degrees Centigrade under Ar after which 0.16 mL of oleic acid, 0.17 mL of oleyl amine, and 0.13 mL of $Fe(CO)_5$ were added. The mixture was heated to 300 degrees Centigrade and refluxed for 30 minutes and allowed to cool to room temperature. FePt nanoparticles were purified in a similar fashion to the Co nanoparticles Nanoparticle Synthesis of CoPt. Preparation was identical to FePt, except 0.16 g of $CO_2(CO)_8$ was substituted for 0.13 mL of $Fe(CO)_5$.

Nanoparticle Synthesis of SmCo5. An arrested precipitation approach was taken to prepare nanoparticles of SmCo5. This technique was adapted from previous efforts at preparing nanoparticles. 38.75 mg of $CoCl_2$ was mixed with 16.0 mg of $SmCl_3$ and dissolved in 20 mL of phenyl ether. 0.357 mL of oleic acid was then added to the mixture, which was then heated to 100 degrees Centigrade under Ar. 1.35 mL of trioctylphosphine was then added. The mixture was then exposed to vacuum for ten minutes to remove any remaining dissolved $O_2$ or $H_2O$ from solution. After purging the solution with vacuum, it was heated to a 290 degrees Centigrade to boil the phenyl ether. 1 mL of superhydride solution was then added. The solution turns from blue to black immediately. The black mixture was then refluxed for 20 minutes and allowed to cool to room temperature Film Formation. To prepare films for phage display selection, a colloidal solution of nanoparticles was drop coated onto a Si slide. The solvent was allowed to evaporate. In the case of FePt and CoPt, the slides were then annealed at 700 degrees Centigrade for 30 minutes under $N_2$ to form the L10 phase. XRD analysis was performed on all of these slides to ensure they were the proper material.

Peptide Selection. The use of a phage display library technique was used to find peptides that bind exclusively to ε-Co, and the L10-phase of CoPt and FePt. Specifically, the Ph.D.-12(tm) and Ph.D.-7 CTM Phage Display Peptide Library Kits were used beginning with 1 μL (or an initial amount) of phage display library to initiate selection against the magnetic substrates (in 1 mL of TBS). For ε-Co, selections were performed in a 10 mM solution of $NaBH_4$ in TBST. After five rounds of panning, peptides and DNA of the peptides were isolated and sequences were obtained from the University of Texas DNA Core Facility. These sequences, which correspond to the peptides displayed on the bacteriophage, underwent analysis to determine consensus sequences. Analysis of the DNA sequences consisted of percent abundance of amino acid per position. Because of the possibility of non-specific binding in the first two rounds, analysis was only performed on the last three rounds of panning.

Binding Affinity. To determine that the peptides bind specifically to ε-Co, CoPt, and FePt, binding affinity was determined. Titer counts were obtained from consensus peptide panning studies and compared to titer counts of WT and random peptides not raised to ε-Co, CoPt, and FePt. Panning studies were then performed using varying concentrations of phage to determine the binding constant of the phage to the metallic surface of interest.

Peptide-Mediated Nucleation of Co. Approximately 880 ul of $H_2O$ were mixed with 100 μL of 1 mM $CoCl_2$ and 20 μL of phage solution (pfu=1011). The mixture was gently agitated for 30 minutes, and then 100 μL of 100 mM $NaBH_4$ was added. The solution was vortexed, and allowed to incubate for another 5 minutes. 100 mL of a solution of TOPO and oleic acid dissolved in $CH_2Cl_2$ was then added. The mixture was vortexed and gently agitated for 1 hour. Over this time period the $CH_2Cl_2$ layer changed to dark grey. This was repeated with several different phage, including Co-1, Co-2, wild type phage, and a TBS solution containing no phage.

Peptide-Mediated Nucleation of CoPt. For nucleation, 50 μL of 1 mM $CoCl_2$ solution was mixed with 50 μL of 1 mM $H_2PtCl_6$ solution. 10 ml of phage solution was then added (pfu=1011). The mixture was agitated gently for 30 min, and 20 μL of 100 mM $NaBH_4$ was then added. The solution was immediately vortexed and placed on a tumbler for 30 min. The final solution was yellow in color.

Peptide-Mediated Nucleation of FePt. FePt was prepared in a similar fashion to CoPt, except a $FeCl_2$ solution was used in place of $CoCl_2$.

Peptide-Mediated Nucleation of SmCo5. Identical to Co synthesis except 100 μL of 1 mM $CoCl_2$ was replaced with 16.7 μL of 1 mM $SmCl_3$ and 83 ul of 1 mM $CoCl_2$.

P8 Expression of Peptides. Genetically modified *E. coli* were amplified overnight in 20 mL LB media, diluted 1:100 and then grown to O.D.=0.6. Tetracycline-HCl (1000×) and 100 mM IPTG was added to a final concentration of 1 mM. The IPTG triggers the production of the modified p8 protein within the cell for their incorporation into the viral coat during assembly. The mixture is allowed to rest for 1 hour without shaking. Infection by the helper phage after 1 hour is then followed by shaking overnight at 39 degrees Centigrade. Phage are then separated and purified by centrifugation and PEG precipitation. The amplified phage pellet is resuspended into 10 mL of TBS (pH 7.5) and dialyzed in 18 MW water. 0.5 mL of both 5 mM $CoCl_2$ and 5 mM $H_2PtCl_6$ is added to 1 mL of amplified phage stock which has been spun down and the supernatant removed. This is allowed to shake for 60 minutes, after which 0.5 mL of 100 mM $NaBH_4$ is added as a reducing agent.

TEM images of the nanoparticles were taken along with the selected area electron diffraction pattern that showed many bands corresponding to the expected values for the CoPt facets. An STEM image of one of these phage with CoPt nanoparticle grown along its P8 proteins was also taken. The length of this structure correlates to the length of a phage (800 nm). FIG. 14A depicts the TEM image of the nanoparticles, and FIG. 14B the resolution image with the selected area electron diffraction pattern (FIG. 14C) showing many bands corresponding to the expected values for the CoPt facets. The STEM image of one of these phage with CoPt nanoparticles grown along its P8 proteins is shown in FIG. 14D. The EDS mapping for Pt (FIG. 14E) and Co (FIG. 14F) indicate that Co and Pt are both found along the length of the structure in equal concentrations.

The present invention illustrates phage display may be used to identify peptides that bind to magnetic materials. The identification is rapid and cost-effective and requires few additional materials. These peptides may then be used to control the nucleation of magnetic nanoparticles, granting the user control over the size, composition, and crystallinity of the resulting nanoparticles. These peptides allow the synthesis of nanoparticles under ambient conditions, making them a desirable alternative to current synthetic strategies.

Phage display libraries and experimental methods for using them in biopanning are further described, for example, in the following U.S. patent publications to Belcher et al.:

(1) "Biological Control of Nanoparticle Nucleation, Shape, and Crystal Phase"; 2003/0068900 published Apr. 10, 2003;

(2) "Nanoscale Ordering of Hybrid Materials Using Genetically Engineered Mesoscale Virus"; 2003/0073104 published Apr. 17, 2003;

(3) "Biological Control of Nanoparticles"; 2003/0113714 published Jun. 19, 2003; and (4) "Molecular Recognition of Materials"; 2003/0148380 published Aug. 7, 2003.

Applications of the present invention, including methods of use, are described in the following references.

Use of superparamagnetic materials in magnetic resonance imaging is described in, for example, U.S. Pat. No. 5,262,176 to Palmacci et al. (Nov. 16, 1993), including use of colloids and superparamagnetic metal oxide covered with a polymer, which is hereby incorporated by reference in its entirety. Superparamagnetic materials are also described in, for example, Lee Josephson et al., *Bioconjugate Chem.*, 1999, 10, 186-191, including biocompatible dextran coated superparamagnetic iron oxide particles derivatized with a peptide sequence, and is hereby incorporated by reference in its entirety. Applications include magnetic resonance imaging and magnetic separations. J. Manuel Perez et al., *J. Am. Chem. Soc.*, 2003, 125, 10192-10193, describes viral-induced self-assembly of magnetic nanoparticles for use in magnetic nanosensors, including MRI, capable of detecting a variety of targets including nucleic acids and proteins. This reference is incorporated by reference in its entirety.

Finally, surfaces can be patterned by a variety of methods known in the art including microlithography and nanolithography and use of resists and self-assembled monolayers, including functionalized self-assembled monolayers.

Although making and using various embodiments of the present invention are discussed in detail below, it will be appreciated that the present invention provides many applicable inventive concepts that can be embodied in a wide variety of specific contexts. The specific embodiments discussed herein are merely illustrative of specific ways to make and use the invention, and do not delimit the scope of the invention.

---

What is claimed is:

1. A method of identifying a peptide that binds to a metal nanoparticle comprising:
   a. preparing a peptide library of 7-12 residues in length expressed or displayed on the surface of phage;
   b. contacting said peptide library with a metal nanoparticle selected from at least one of Co, CoPt, $SmCo_5$ or FePt;
   c. eluting the peptide that specifically binds to the metal nanoparticle and wherein the peptide nucleates the nanoparticle;
   d. repeating steps b and c at least once; and
   e. isolating the peptide.

2. The method of claim 1, wherein the metal nanoparticle comprises Co.

3. The method of claim 1, wherein the metal nanoparticle comprises CoPt.

4. The method of claim 1, wherein the metal nanoparticle comprise $SmCo_5$.

5. The method of claim 1, wherein the metal nanoparticle comprises FePt.

6. The method of claim 1, wherein the phage is M13 bacteriophage.

7. The method of claim 1, wherein the contacting occurs at room temperature.

* * * * *

UNITED STATES PATENT AND TRADEMARK OFFICE
CERTIFICATE OF CORRECTION

| | |
|---|---|
| PATENT NO. | : 7,374,893 B2 |
| APPLICATION NO. | : 11/778713 |
| DATED | : May 20, 2008 |
| INVENTOR(S) | : Angela M. Belcher et al. |

It is certified that error appears in the above-identified patent and that said Letters Patent is hereby corrected as shown below:

Col. 1, lines 16-17, "may own certain rights" should be --has certain rights--.

Signed and Sealed this

First Day of December, 2009

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,374,893 B2 | Page 1 of 1 |
| APPLICATION NO. | : 11/778713 | |
| DATED | : May 20, 2008 | |
| INVENTOR(S) | : Angela M. Belcher et al. | |

It is certified that error appears in the above-identified patent and that said Letters Patent is hereby corrected as shown below:

In the Specification

Col. 1, lines 14-17, should be corrected as follows:

This invention was made with government support under Grant no. DAAD19-99-1-0155 awarded by the Army Research Office. The government has certain rights in the invention.

Signed and Sealed this
Twenty-first Day of July, 2015

Michelle K. Lee
*Director of the United States Patent and Trademark Office*